US011213626B2

(12) United States Patent
Paramanandam et al.

(10) Patent No.: US 11,213,626 B2
(45) Date of Patent: Jan. 4, 2022

(54) AUTOINJECTOR WITH STALL AND END POINT DETECTION

(71) Applicant: AMGEN INC., Thousand Oaks, CA (US)

(72) Inventors: Sivakumar Paramanandam, Newbury Park, CA (US); Andrew Coles, Thousand Oaks, CA (US); Nicola Alagia, Milan (IT); Antonio Antonini, Milan (IT)

(73) Assignee: AMGEN INC., Thousand Oaks, CA (US)

( * ) Notice: Subject to any disclaimer, the term of this patent is extended or adjusted under 35 U.S.C. 154(b) by 413 days.

(21) Appl. No.: 16/188,496

(22) Filed: Nov. 13, 2018

(65) Prior Publication Data
US 2019/0143044 A1    May 16, 2019

Related U.S. Application Data

(60) Provisional application No. 62/587,421, filed on Nov. 16, 2017.

(51) Int. Cl.
| A61M 5/24 | (2006.01) |
| A61M 5/31 | (2006.01) |
| A61M 5/315 | (2006.01) |
| A61M 5/145 | (2006.01) |
| A61M 5/20 | (2006.01) |
| A61M 5/32 | (2006.01) |

(52) U.S. Cl.
CPC .............. *A61M 5/24* (2013.01); *A61M 5/145* (2013.01); *A61M 5/20* (2013.01); *A61M 5/3135* (2013.01); *A61M 5/3157* (2013.01); *A61M 5/31545* (2013.01); *A61M 5/322* (2013.01); *A61M 2005/2006* (2013.01)

(58) Field of Classification Search
CPC .......... A61M 5/24; A61M 5/145; A61M 5/20; A61M 5/3135; A61M 5/3157; A61M 5/31545; A61M 5/322; A61M 2005/2006
See application file for complete search history.

(56) References Cited

U.S. PATENT DOCUMENTS

| 8,052,645 B2 | 11/2011 | Slate et al. |
| 8,177,749 B2 | 5/2012 | Slate et al. |
| (Continued) | | |

FOREIGN PATENT DOCUMENTS

| CN | 102762241 A | 10/2012 |
| EP | 2468340 A1 | 6/2012 |
| (Continued) | | |

OTHER PUBLICATIONS

International Application No. PCT/US2018/060264, International Search Report and Written Opinion, dated Feb. 12, 2019.
(Continued)

*Primary Examiner* — Amber R Stiles
(74) *Attorney, Agent, or Firm* — Marshall, Gerstein & Borun LLP

(57) ABSTRACT

An autoinjector drug delivery device configured with a stall and endpoint detection algorithm is described that allows for variations in the fill of the drug, barrel, plunger, and other components. The stall or end point detection causes the autoinjector to stop an extrusion process.

19 Claims, 23 Drawing Sheets

(56) References Cited

U.S. PATENT DOCUMENTS

| | | | |
|---|---|---|---|
| 2005/0020980 A1* | 1/2005 | Inoue | A61M 39/10 |
| | | | 604/152 |
| 2011/0160666 A1 | 6/2011 | Hanson et al. | |
| 2012/0101439 A9 | 4/2012 | Slate et al. | |
| 2013/0274655 A1* | 10/2013 | Jennings | A61M 5/24 |
| | | | 604/67 |
| 2016/0213842 A1* | 7/2016 | Eggert | A61M 5/145 |

FOREIGN PATENT DOCUMENTS

| | | |
|---|---|---|
| WO | WO-2005/000378 A2 | 1/2005 |
| WO | WO-2008/140546 A2 | 11/2008 |
| WO | WO-2012/145685 A1 | 10/2012 |
| WO | WO-2012/160160 A1 | 11/2012 |
| WO | WO-2015/036359 A1 | 3/2015 |

OTHER PUBLICATIONS

European U.S. Appl. No. 18/816,316, Communication Pursuant to Article 94(3) EPC, dated Apr. 12, 2021.
European Patent Application No. 18816316, Communication Pursuant to Article 94(3) EPC, dated Sep. 22, 2021.
Chinese Patent Application No. 201880068980.5, First Office Action, dated Sep. 17, 2021.

\* cited by examiner

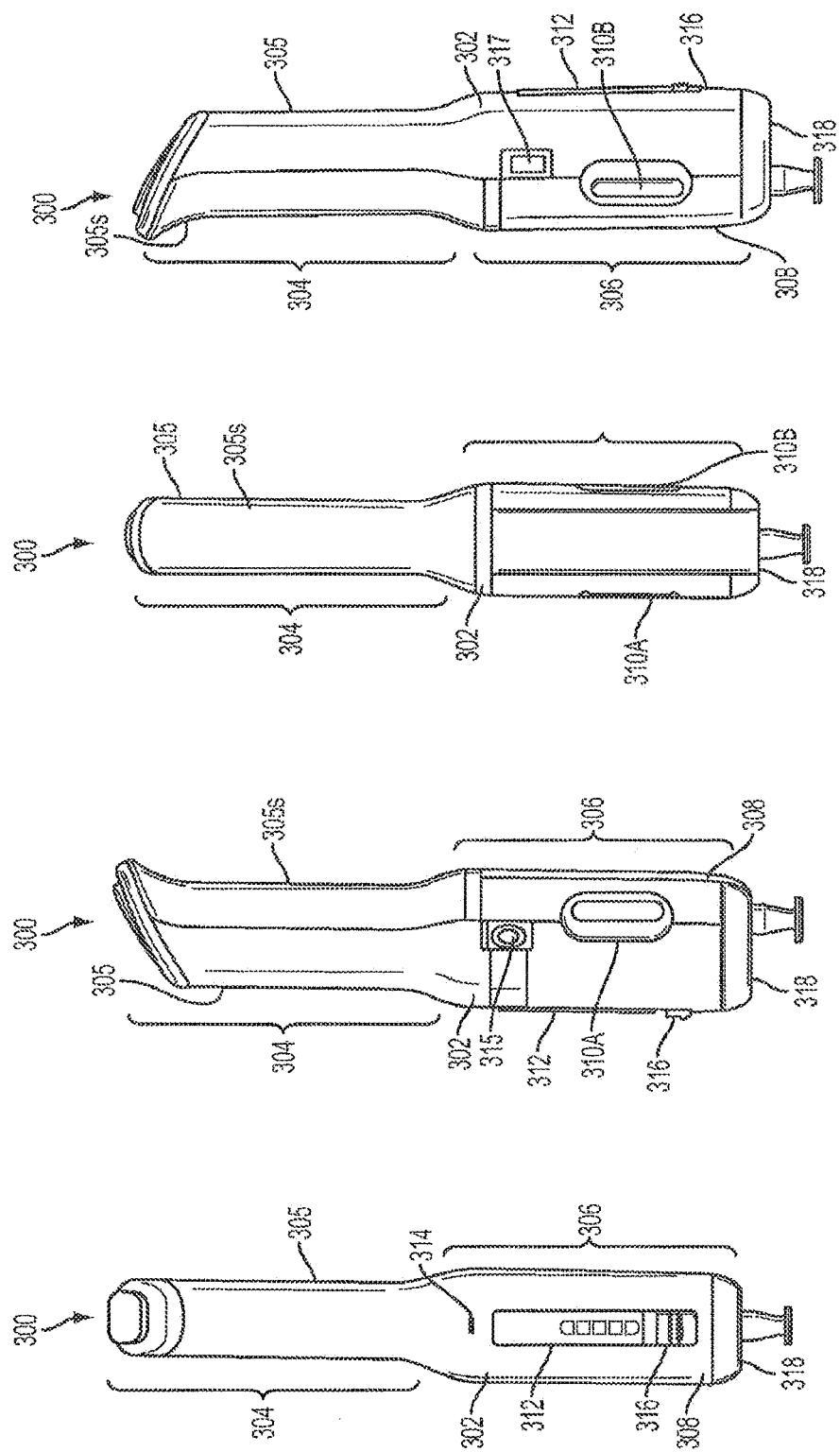

AUTOINJECTOR WITH STALL AND END POINT DETECTION

CROSS-REFERENCE TO RELATED APPLICATION

The priority benefit of U.S. Provisional Patent Application No. 62/587,421, filed Nov. 16, 2017, is claimed, and the entire contents thereof are expressly incorporated herein by reference.

FIELD OF THE DISCLOSURE

The disclosure relates to injection systems and apparatus. More particularly, the disclosure relates to operation of an autoinjector apparatus.

BACKGROUND

Pre-filled hypodermic syringes can be used for home-use because they may be prepared with a required dosage of a pharmaceutical product and are operated by merely advancing the stopper of the syringe. Aside from the costs of the particular medication used, pre-filled syringes may be economically manufactured.

Nevertheless, pre-filled syringes can have drawbacks. Specifically, many users are either frightened by an exposed injection needle or feel they are inherently incapable of performing an injection. Because of aversions to exposed needles, as well as health and safety issues that may be involved, various types of injectors and other devices have been developed for concealing needles from the user and automating the injection task to assist the user in performing the injection, ensure reliable delivery of the medication and ensure patient safety. See the following patents or patent applications, which are each herein incorporated by reference in its entirety: U.S. Pat. Nos. 8,052,645 and 8,177,749; U.S. Publ. No. 2012/0101439; and PCT Publ. No. WO 2012/145685.

Typically, three tasks may be performed when injecting a drug into a patient with a hypodermic syringe: 1) insertion of the needle into the patient; 2) injection of the drug from the syringe into the patient; and 3) withdrawal of the needle after the injection has been completed. For each task, the magnitude and direction of forces on the syringe, as well as the location of their application, may be different from the other tasks. For example, insertion of the needle may require the application of a minimal force on the syringe, for a very short period of time. On the other hand, injection of the medicament may require the application of a much greater force on the plunger of the syringe, and this force may need to be applied for a relatively longer period of time. Further, needle withdrawal may require the application of a force in an opposite direction from needle insertion. These, and other similar considerations, may become relevant when the injection process is to be automated.

In addition to these mechanical considerations, the design of an autoinjector may require user-friendly considerations. In particular, it may be desirable for the injection needle of the syringe to be operationally concealed from the view of a user. Preferably, this concealment is maintained before, during and after an injection procedure. Further, it may be desirable that operation of the syringe be limited to only those times when the syringe is properly positioned for an injection and/or when the appropriate sequence of actions are performed by the user.

When subcutaneously injecting a drug, patients may desire a swift, but smooth and steady injection. The length that the needle is disposed within the patient is balanced against the feel of the drug flow entering into the subcutaneous space. In one form, drug delivery devices can determine that a dose of drug has been dispensed by moving a plunger rod to a fixed, end position from a starting position. Moving to such a fixed position, however, can leave some drug within the syringe if too conservative or can break the glass of the syringe if too aggressive. Further, if the plunger stalls in the middle of an extrusion before the plunger rod reaches the end position, the plunger rod can embed in or bypass the plunger in an attempt to get to the end position. Additionally, in closed loop feedback systems, stall detection is more difficult where consistent injection speed is the aim.

A plunger can stall due to any number of circumstances. For example, manufacturing variations in anything from fill volume, plunger installation location, plunger composition or temperature for compression thereof, siliconization of the plunger or syringe, syringe tapering or shape, motor capability, battery performance effecting injection speed, and so forth can cause variations in extrusion speeds over the injection process. Additionally, conditions can effect extrusion speeds, such as temperature of the drug affecting the viscosity thereof, local heating in the windings of the motor causing engine performance degradation.

SUMMARY

A drug delivery device is described herein that includes a reservoir configured to contain a drug and that has a first end and a second end, a plunger disposed within the reservoir at the first end thereof, where the plunger is slidingly movable within the reservoir. The device further includes a plunger rod configured to engage the plunger, a motor operably coupled to the plunger rod and configured to drive the plunger rod to thereby slide the plunger from the first end of the reservoir to the second end of the reservoir, and an encoder coupled to the motor. The device further includes a controller that is configured to receive signals from the encoder, determine whether the plunger has stopped moving within the reservoir based on the signals, and stop operation of the motor in response to determining that the plunger has stopped moving for a predetermined amount of time.

In various embodiments, the encoder can include a disk having one or more discernible portions and an optical sensor configured to detect the discernible portions and send a signal in response to the detection.

In various embodiments, the drug delivery device can further include a needle and a needle insertion mechanism, and the controller can be configured to retract the needle in response to determining that the plunger has stopped moving for the predetermined amount of time.

A method is described herein for operating a drug delivery device. The method includes receiving signals at a controller from an encoder coupled to a motor of the drug delivery device, the motor operably coupled to a plunger rod configured to engage and drive a plunger within a reservoir, determining whether the plunger has stopped moving within the reservoir with the controller based on the signals, and stopping operation of the motor with the controller in response to determining that the plunger has stopped moving for a predetermined amount of time.

In various embodiments, the method can further include detecting a discernible portion of a disk of the encoder with an optical sensor, and sending a signal in response to the detection.

In various embodiments, the method can further include sampling the position of the plunger rod at set intervals with the controller by determining a current count of the signals.

In various embodiments, determining whether the plunger has stopped moving within the reservoir can include determining whether the signals indicate that the plunger has moved within the last predetermined number of samples. In further embodiments, the method can further include comparing the current count to an expected endpoint count corresponding to the plunger being driven to the second end of the reservoir. In yet further embodiments, the method can include revising the predetermined number of samples in response to determining that the current count is less than the expected endpoint. In further embodiments, the method can include determining that the plunger has stalled before being driven to the second end of the reservoir in response to determining that the current count is less than the expected endpoint.

In various embodiments, the method can further include retracting a needle of the drug delivery device with a needle insertion mechanism in response to the controller determining that the plunger has stopped moving for the predetermined amount of time.

It should be noted that while the specification frequently refers to an autoinjector, in various embodiments the device may also be referred to as an injector. Reference to an autoinjector is often associated with a patient providing an injection to themselves, however, such an injection may also be administered by a health care provider. Similarly, use of an injector may be undertaken by either the patient or health care provider.

BRIEF DESCRIPTION OF THE DRAWINGS

The accompanying figures show embodiments according to the disclosure and are exemplary rather than limiting.

FIG. 2A is a front view of the autoinjector apparatus of FIG. 1 showing the cassette installed in the autoinjector.

FIG. 2B is a side view of a first side of the autoinjector apparatus of FIG. 1 showing the cassette installed in the autoinjector.

FIG. 2C is a rear view of the autoinjector apparatus of FIG. 1 showing the cassette installed in the autoinjector.

FIG. 2D is side view of a second side of the autoinjector apparatus of FIG. 1 showing the cassette installed in the autoinjector.

DETAILED DESCRIPTION

Figure 1:
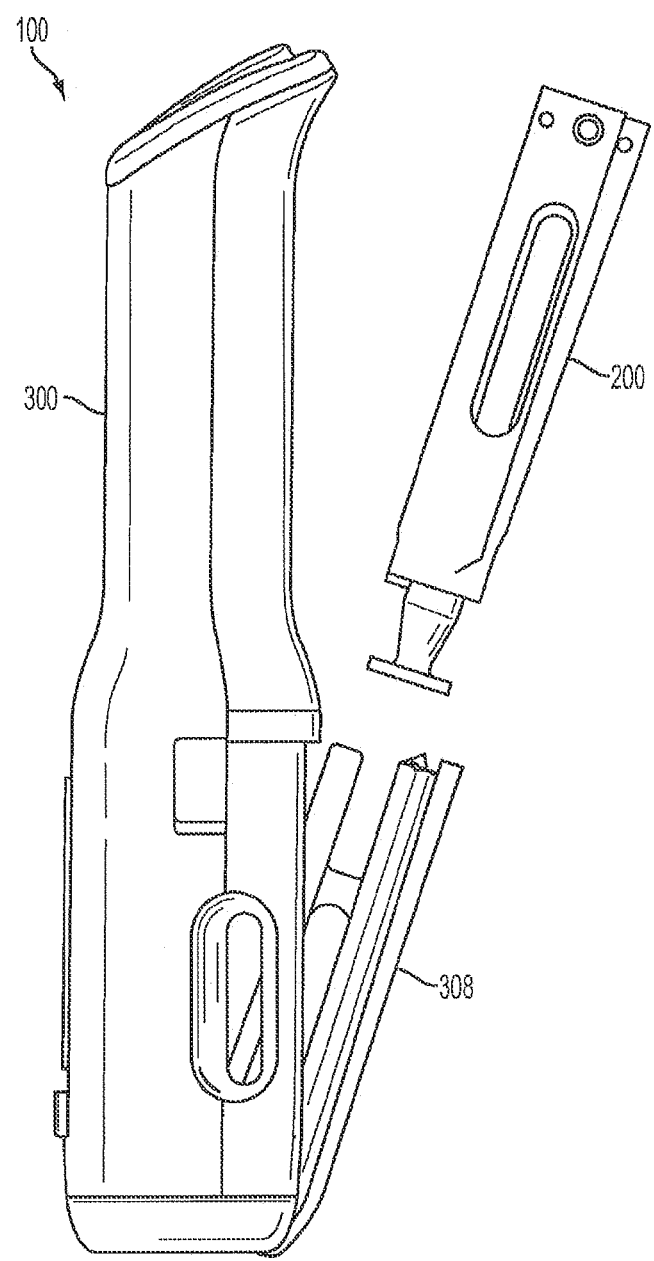
FIG. 1 is a side view of an embodiment of an autoinjector apparatus comprising a cassette and an autoinjector, showing the cassette prior to installation in the autoinjector.

FIG. 1 shows an embodiment of an autoinjector system or apparatus 100 that can be used for injecting a dose of pharmaceutical product (drug) into a patient, the injection often being self-administered by the patient (user). Alternatively, the drug can be administered by a health-care provider. As shown, the autoinjection system or apparatus 100 may comprise a removable cassette 200 and an autoinjector or injector 300. Various embodiments of the cassette 200 may be constructed to contain a drug to be injected into the user by the autoinjector 300. In various other embodiments the cassette 200 may be constructed for use in training the user to operate the autoinjector 300 (a training cassette). The autoinjector 300 may be constructed to deliver an injection automatically upon actuation by the user or some other person. Various embodiments of the autoinjector 300 may have a cassette door 308 that can be constructed to pivot between and an open position and a closed position to allow insertion of the cassette 200 into the autoinjector 300. In some embodiments, the cassette door 308 may include a "cassette" icon (not shown) that indicates the insertion entry point for the cassette 200.

Referring collectively to FIGS. 2A-2F, various embodiments of the autoinjector 300 may comprise a casing 302 having a handle section 304 and a cassette receiving section 306 inline with the handle section 304. To aid patients with manual dexterity issues, the handle section 304 of the autoinjector casing 302 may define an ergonomically shaped handle 305 with a soft grip area 305S. The cassette receiving section 306 comprises the cassette door 308 (FIGS. 2B and 2D) described earlier. The cassette door receives the cassette 200 in an open position (FIG. 1) and aligns the cassette 200 with insertion and extrusion drives, and other structures and components of the autoinjector 300 in a closed position. The cassette door 308 may include a "cassette" icon that indicates the insertion entry point for the cassette 200. The cassette receiving section 306 of the casing 302 may comprise windows 310A, 310B on sides thereof that align with windows of the cassette 200 when the cassette door 308 is closed with the cassette 200 correctly installed therein. In one or more embodiments, the windows 310A, 310B may be double-layered. One or more lights (not shown) may be provided inside the casing 302 to evenly backlight illuminate the cassette windows 212 (FIG. 5A) and the syringe 260 disposed within the inner sleeve 220 of the cassette 200 (FIG. 5B), so that the user can observe the injection cycle through the windows 310A, 310B of the autoinjector 300, i.e., observe the initial and end positions of the plunger-stopper 264 of the syringe 260 (FIG. 5B) during the syringe content (hereinafter "drug") extrusion process, as well as syringe movements within the cassette 200.

Referring still to FIGS. 2A, 2B, 2D, and 2F, the autoinjector 300 may further comprise a user interface 312 and an audio speaker (not shown). The user interface 312 (best illustrated in FIG. 2A) may be located in the cassette receiving section 306 of the casing 302, and provides various visual indicators. The audio speaker may be disposed inside the casing 302 and provides various audible indicators. The audio speaker may audibly communicate with the external environment via a speaker aperture 314 formed in the casing 302 in the cassette receiving section 306. The visual and audible indicators generated by the user interface 312 and the audio speaker can tell the user when the autoinjector 300 is ready for use, the progress of the injection process, injection completion, the occurrence of any errors, and other information. The autoinjector 300 may further comprise one or more of a settings/mute switch 315, a speed selector switch 316, a start button 307, and an eject button 317. The settings/mute switch 315 (FIG. 2B) may be located in the cassette receiving section 306 of the casing 302. The mute switch 315 may be constructed allow the user to turn on and off all synthesized sounds, except error sounds, and to respond in real-time so that if the user begins the injection process and changes the mute switch to off, the sounds are immediately muted. The mute switch 315 may also be constructed to slide toward a "mute" icon to mute the audio speaker. A light indicator may be provided to confirm the "mute" state. The speed selector switch 316 (FIGS. 2A and 2B) may be located in the cassette receiving section 306 of the casing 302. The speed selector switch 316 may be constructed to allow the user to select among a plurality of preset drug delivery (extrusion) speeds to accommodate personal patient preference. The speed selector switch 316 may comprise a three switch positions. Other embodiments of the speed selector switch may comprise two switch positions, or 4 or more switch positions. In still other embodiments, the speed selector switch may be of the infinitely variable type. In some embodiments, changing the position of the switch 316 prior to injection changes the speed of drug extrusion during injection while changing the position of the speed selector switch 316 during injection, does not change the speed of the injection in real time. The autoinjector 300 may also be provided with one or more demo cassettes to allow the user to experiment with different speeds of drug delivery. The start button 307 may be disposed at a free end of the handle 305. The button 307 may include an indentation 307i (FIG. 2F) for optimizing thumb placement on the button 307. The button 307 may be made of a translucent material that allows a lighting effect to illuminate the button as signals. The eject button 317 (FIG. 2D) may be located in the cassette receiving section 306 of the casing 302. The eject button 317 may include an indentation 317i for optimizing finger placement on the button 317. In some embodiments, the eject button 317 may be controlled by a microprocessor 350 (FIG. 2H) of the autoinjector 300, which may be programmed to eliminate accidental inputs during the injection process.

Figure 2E:
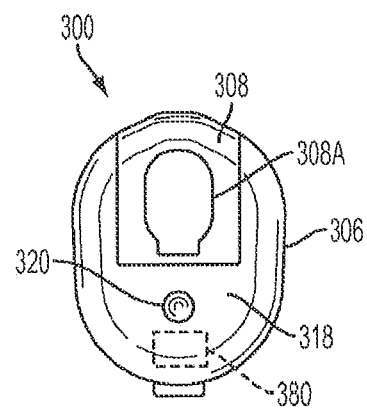
FIG. 2E is an end view of a first end of the autoinjector of the autoinjector apparatus of FIG. 1.
Figure 2F:
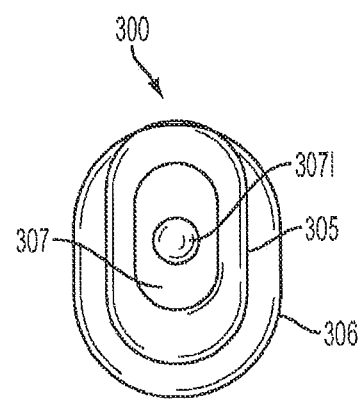
FIG. 2F is an end view of a second end of the autoinjector of the autoinjector apparatus of FIG. 1.

Referring to FIG. 2E, the cassette receiving section 306 of the casing 302 and the cassette door 308 may form a proximal end wall 318 of the autoinjector 300. The proximal end wall 318 may be configured as a broad, flat and stable base for easily positioning the autoinjector 300 on a support surface, after removal of the shield remover 240 (FIG. 5A) or when the autoinjector 300 does not contain the cassette 240. The portion of the proximal end wall 318 formed by the cassette door 308 may include an aperture 308A that is sized and shaped to allow the shield remover 240 to be removed from the cassette 200 and withdrawn through the aperture 308A, when the cassette 200 is installed in the autoinjector 300. The proximal end wall of the autoinjector 300 may further comprise a target light 320. The target light 320 may be constructed to turn on when the shield remover 240 is removed from the cassette 200 and withdrawn through the aperture 308A, thereby visually indicating that the shield remover 240 has been removed. Once turned on, the target light aids the user in visualizing and selecting an injection site.

Referring still to FIG. 2E, the autoinjector 300 may further comprise a capacitance-based skin sensor 380 (shown with broken lines) or any other suitable skin sensor. The skin sensor 380 may coupled to a microprocessor provided, for example, in the autoinjector 300 in a manner that allows signals or data to be communicated to the microprocessor, so that the autoinjector 300 can determine when the proximal end wall 318 of the autoinjector 300 touches or contacts skin without the need to provide downward pressure on the injection-site area. The skin sensor 380 may also be constructed to inform the user through audible and visual indicators generated by the speaker and user interface, when skin contact is detected. In some embodiments, the skin sensor 380 may comprise two pads or electrodes (not shown) located adjacent to an inner surface of or embedded in the proximal end wall 318 of the autoinjector 300. When the proximal end wall 318 is placed in contact with the skin, the electrode's capacitance signal increases. If the increase is sufficient as determined by the microprocessor, which may be programmed with sensor decision logic, that electrode will become activated. To determine whether skin contact has been made, the microprocessor reads the capacitance of the electrodes. The microprocessor then processes the capacitance information from both electrodes to determine when the proximal wall 318 makes proper contact with the skin. In the embodiment where the electrodes are disposed on the inner surface of the proximal wall 318, the electrodes themselves never make contact with skin, only the plastic housing makes contact with skin, with the electrodes attached to the housing on the inside. Such a design would account for the distance of the electrodes from the skin (spaced by the proximal wall 318) as well as the housing material response in how the calculation determines that the device is in contact with (or in actuality just very close to) the injection site.

Figure 2G:
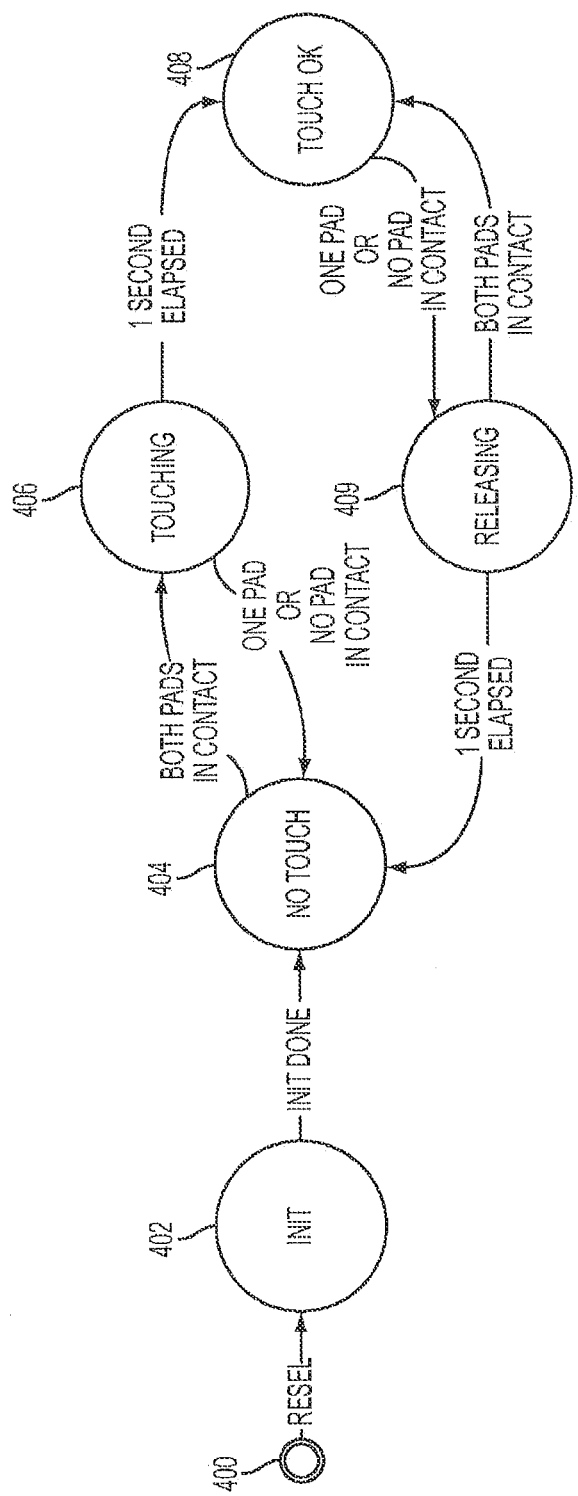
FIG. 2G is a state diagram showing an embodiment of the decision logic for controlling a skin sensor of the autoinjector apparatus of FIG. 1.

FIG. 2G is a state diagram illustrating the decision logic for controlling skin sensor 380 with the microprocessor of the autoinjector 300, according to an embodiment of the present disclosure. The process starts at 400 which represents a reset of the autoinjector. The logic then flows to state 402 which represents the initialization of the skin sensor after the reset of the autoinjector. Once initialized, the logic flows to state 404 which represents a "no-touch" state where none or only one of the electrodes of the sensor sense that the proximal end wall 318 touches the skin. If both electrodes sense that the proximal end wall 318 touches skin for less than a certain threshold time period (e.g., one second), the logic flows to state 406 which represents a "touching" state. If one or neither one of the electrodes sense that the proximal end wall 318 touches skin, the logic flows back to state 404. If, however, both electrodes sense that the proximal end wall 318 touches skin for a period of time equal to the threshold time period (e.g., one second), the logic flows to state 408 which represents a "touch OK" state. If one electrode or no electrodes sense that the proximal end wall 318 contacts skin, the logic flows to a "releasing" state 409. If both electrodes touch skin, the logic flows back to "touch OK" state 408. If one or no electrodes contact skin for more than the threshold time period (e.g., more than one second), the logic flows back to "no touch" state 404.

In a further approach, the autoinjector 300 can include multiple sensors 380 so that the microprocessor 350 can analyze the capacitance measured by each sensor 380. Correct positioning of the autoinjector 300 can be determined, in this embodiment, by a predetermined level of capacitance in each sensor 380 for a predetermined amount of time. Further, based on continually reading or periodically sampling the capacitance levels of each sensor 380, the microprocessor 350 can determine if one or more sensors 380 are losing capacitance, which could indicate that the user is tilting the injector 300. Thereafter, if a sensor 380 drops below a threshold for a predetermined amount of time, the microprocessor 350 can follow the above logic to reorient the injector 300. This embodiment can help a user operate the autoinjector 300 with reduced errors due to nervousness, tremors, or fidgeting.

Figure 2H:
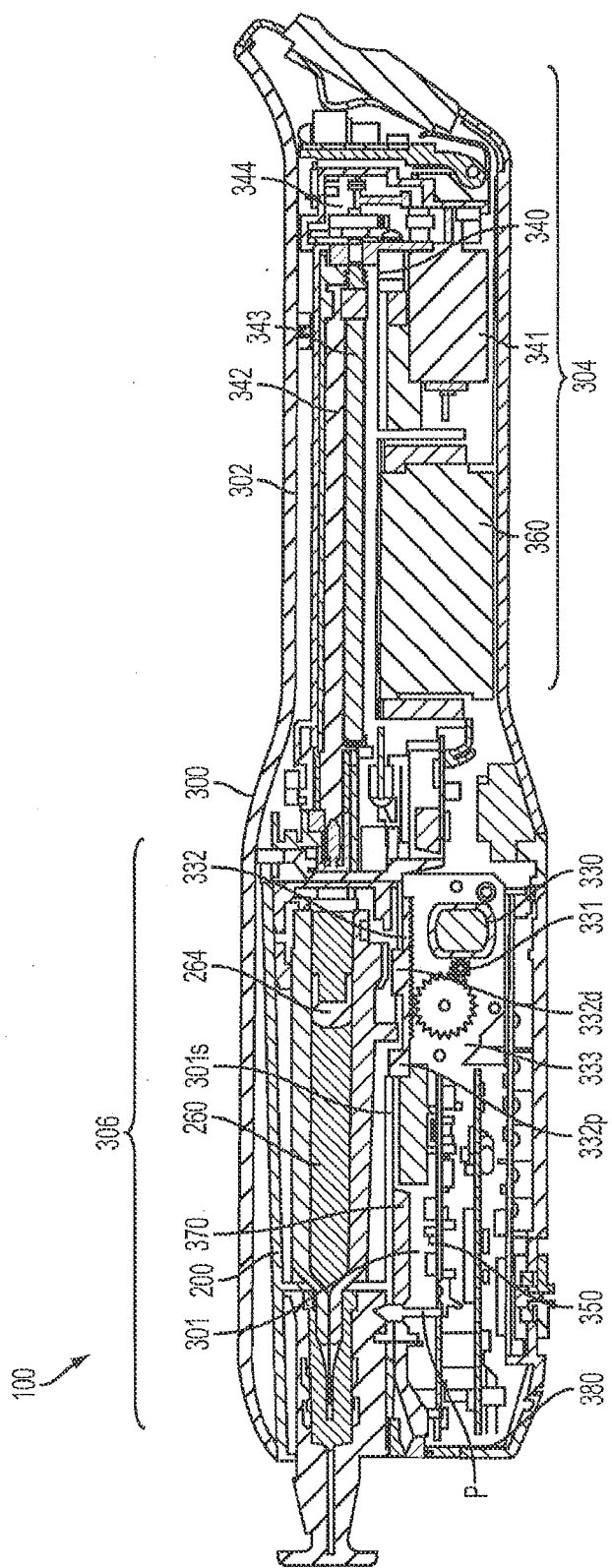
FIG. 2H is a sectional side view of an embodiment of the autoinjector apparatus showing the cassette installed in the autoinjector.

As shown in FIG. 2H, various embodiments of the autoinjector 300 may comprise a chassis 301 disposed in the casing 302 for supporting a motorized needle insertion drive 330, a motorized drug extrusion drive 340, a microprocessor 350, a battery 360 for powering the drives 330, 340 and the microprocessor 350, and the skin sensor 380. The casing 302 may define an ergonomically shaped handle section 304 and a cassette receiving section 306. The chassis 301 may include a support surface 301s for supporting one or more cassettes 200 in the autoinjector 300 and aligning the cassette 200 or a selected one of the one or more cassettes 200 with motorized needle insertion and drug extrusion drives 330 and 340, respectively. A detector 370 may be provided on or in the cassette support surface 301s for sensing the presence of and/or information about the cassette 200. The detector 370 may be coupled with the microprocessor 350 in a manner that allows signals or data to be communicated to the microprocessor 350. The insertion drive 330 may include an insertion rack 332, an insertion drive motor 331 and an insertion drive gear train 333 for transmitting rotary motion of the insertion drive motor 331 to drive the rack 332. The insertion rack may include a tab arrangement including, for example, proximal and distal tabs 332p and 332d, respectively, which interface with the cassette 200. The extrusion drive 340 may comprise an extrusion drive motor 341, a plunger rod 342, a lead screw 343, and an extrusion drive gear train 344. The plunger rod 342 is driven by the extrusion drive motor 341 through the lead screw 343 and the extrusion drive gear train 344, and may interface with a plunger 264 of a drug container 260 contained within the cassette 200. The autoinjector 300 can be used for executing multiple injections.

Referring still to FIG. 2H, the term microprocessor as utilized herein refers broadly to any controller, microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The microprocessor 350 may be configured (for example, by using corresponding programming stored in a memory as will be well understood by those skilled in the art) to carry out one or more of the steps, actions, and/or functions described herein. For example, the microprocessor 350 of the autoinjector 300 may be programmed with instructions that, when executed by the microprocessor 350, enable it to control and monitor the various operations and functions of the autoinjector 300. For example, but not limitation, the microprocessor 350 may be programmed with instructions for controlling the motorized insertion and extrusion drives 330, 340. Such instructions may control and monitor each step of the injection cycle and process flow, thereby automating needle insertion, drug extrusion, and needle retraction, and controlling the sequence of actions performed by the user so that the injection process and drug administration can be made more reliable, accurate, and consistent. The microprocessor 350 may also be programmed with instructions for controlling the audible and visual feedbacks to the user. An automated power-on self-test checks the operation of the autoinjector 300 and remaining battery charge.

In various other embodiments, the autoinjector 300 may include other types of needle insertion drives, drug extrusion drives, and means for activating and sequencing the drives. The insertion and extrusion drives, in such embodiments may be implemented as separate and distinct mechanisms or combined into a single mechanism. The insertion and extrusion drives of such embodiments may be powered, without limitation, by motors, mechanical mechanisms (e.g., elastic members such as springs), gas pressure mechanisms, gas releasing mechanism, or any combination thereof. Various transmission mechanisms may be used for transmitting the power to the cassette, to cause injection of the drug. In addition, the activating and sequencing means may comprise various mechanical and electromechanical arrangements, which may be combined with the microprocessor described earlier or used alone. The autoinjector in such embodiments may be constructed to be reusable for executing multiple injections or be designed for a single, disposable use.

Figure 2I:
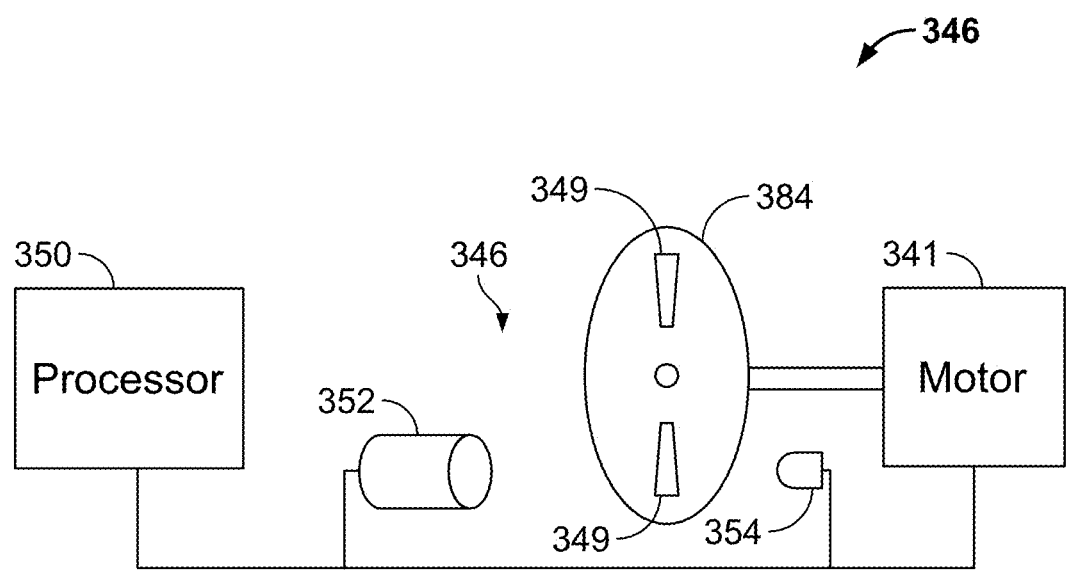
FIG. 2I is a diagrammatic view of a motor and encoder for determining plunger travel distance for the autoinjector apparatus of FIG. 1.

By one approach, the autoinjector 300 may include an encoder 346 coupled to the motor 341 and in communication with the microprocessor 350. The microprocessor 350 receives signals from or queries the encoder 346 to determine a number of rotations of the motor 341 to thereby extrapolate a distance that the plunger rod 342 and plunger 264 have traveled during an extrusion process. The encoder 346 can take any suitable form. In the example illustrated in FIG. 2I, the encoder 346 includes a disk 348 having discernible portions 349 and an optical sensor 352. The disk 348 is coupled to the motor 341 to be rotated thereby and the optical sensor 352 is configured to identify the discernible portions 349 as they are rotated within a sensing area of the sensor 352. The discernible portions 349 can be windows, slits, transparent portions, translucent portions, and so forth. If desired, the encoder 346 can utilize a light source 354 to illuminate the discernible portions 349 so that the sensor 352 can easily detect the discernible portions 349.

Figure 3:
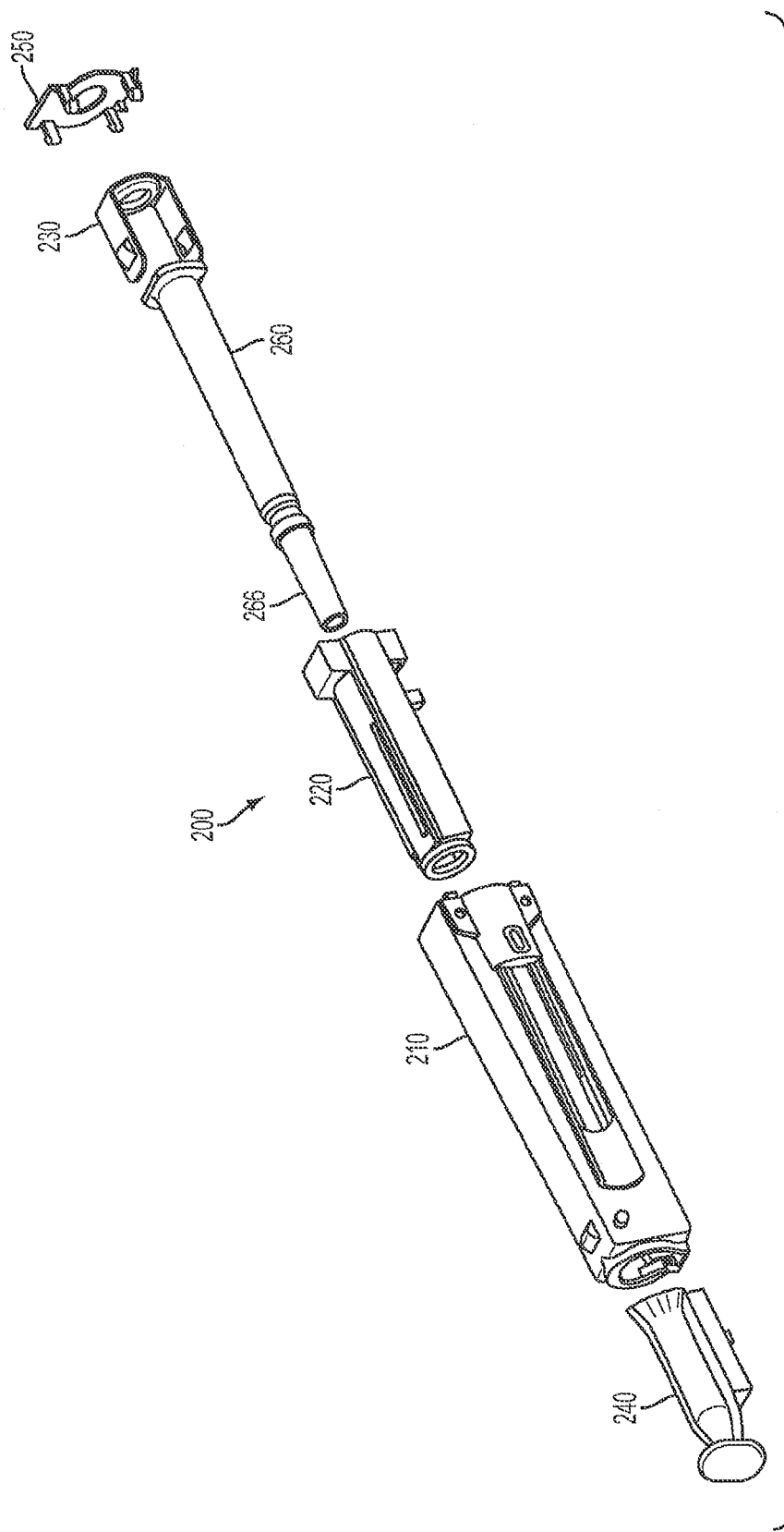
FIG. 3 is an exploded perspective view of an embodiment of the cassette.

Referring now to FIG. 3, various embodiments of the cassette 200 may comprise an outer housing 210, an inner sleeve 220, a drug container 260 for containing a drug, a cassette cap 240, a lock cap 230, and a cover 250. Such embodiments of the cassette 200 facilitate and enable easy injection of the drug with the autoinjector and can be constructed for a single, disposable use. In various embodiments, the lock cap 230 and cover 250 of the cassette 200 may be constructed to resist removal of the drug container 260 from the cassette 200, thereby preventing needle sticks before and after use of the cassette 200 and also preventing the drug container 260 from being taken out of the cassette 200 or replaced. In addition, the lock cap 230 and cover 250 protect the drug container 260 during shipment and transportation. The cassette cap 240, in various embodiments, may be constructed to remove a needle shield 266 covering an injection needle associated with the drug container 260. In various other embodiments, the cassette cap 240 may also be constructed to engage the outer housing 210 of the cassette 200, such that the cassette cap 240 cannot be rotated or twisted, thereby preventing the needle shield 266 from damaging the injection needle. Various embodiments of the inner sleeve 220 may be constructed to position the drug container 260 within the cassette housing 210 in either a needle-concealed position or a needle injection position during an injection cycle of the autoinjector. In various other embodiments, the outer housing 210 and the inner sleeve 220 of the cassette 200 may include one or more locking arrangements that protect the drug container 260 and prevent unintended needle exposure or damage. Various other embodiments of the cassette 200 may include a cassette identification arrangement that interfaces with the autoinjector to communicate the installation of the cassette 200 within the autoinjector and/or information about the cassette 200.

Figure 4:
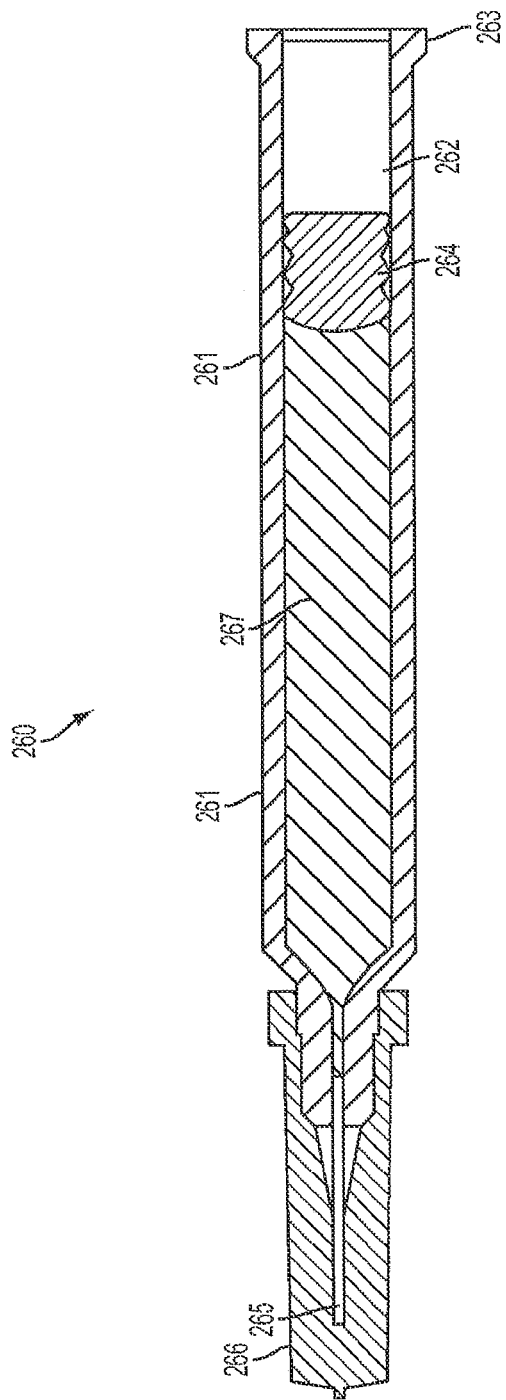
FIG. 4 is a sectional side view of an embodiment of a drug container that can be provided in the cassette.

As shown in FIG. 4, the drug container 260 may comprise a conventional glass or plastic syringe comprising a barrel 261 that defines a fluid chamber 262. The fluid chamber 262 may be filled for treatment or be prefilled with a predetermined dose of a drug 267. The drug may have a viscosity that depends on the temperature of the product. The syringe 260 may further comprise an injection needle 265 removably or fixedly disposed at a proximal end of the barrel 261, and an outwardly extending flange 263 disposed at a distal end of the barrel 261. The injection needle 265 may communicate with the fluid chamber 262 to allow dispensing of the predetermined dose of the drug 267 expelled from the fluid chamber 262 of the syringe barrel 261. The syringe 260 may further comprise a moveable plunger-stopper 264, disposed within the fluid chamber 262 of the barrel 261, for expelling the predetermined dose of the drug 267 from the chamber 262 so that it may be dispensed through the injection needle 265. A protective needle shield 266 made, for example, of a non-rigid material, may be provided for covering the injection needle 265.

In some embodiments, the drug contained in the drug container 260 may have a viscosity of about 19 centipoise, at room temperature (20 to 25° C. [68-77° F.]).

In some embodiments, the drug contained in the drug container 260 may have a viscosity ranging between about 1 centipoise and about 320 centipoise, at room temperature.

In some embodiments, the drug contained in the drug container 260 may have a viscosity ranging between about 5 centipoise and about 40 centipoise, at room temperature.

In some embodiments, the drug contained in the drug container 260 may have a viscosity ranging between about 10 centipoise and about 35 centipoise, at room temperature.

In some embodiments, the drug contained in the drug container 260 may have a viscosity ranging between about 15 centipoise and about 30 centipoise, at room temperature.

In some embodiments, the drug contained in the drug container 260 may have a viscosity ranging between about 20 centipoise and about 25 centipoise, at room temperature.

In some embodiments, the drug contained in the drug container 260 may have a viscosity ranging between about 16 centipoise and about 42 centipoise, at room temperature.

In some embodiments, the drug contained in the drug container 260 may have a viscosity ranging between about 1 centipoise and about 29 centipoise, at room temperature.

Figure 5A:
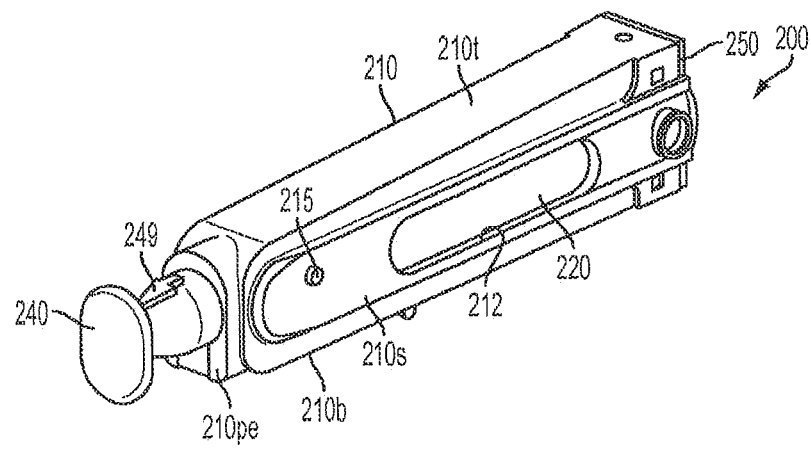
FIG. 5A is a top down front perspective view of an embodiment of the cassette.
Figure 5B:
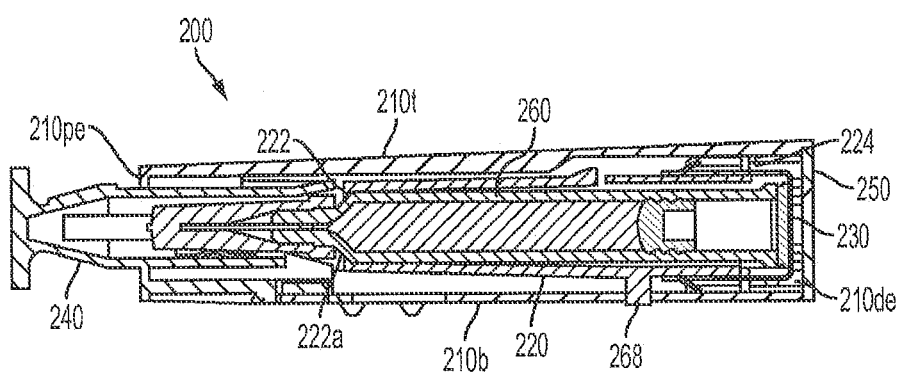
FIG. 5B is a sectional side view of the cassette of FIG. 5A.
Figure 5C:
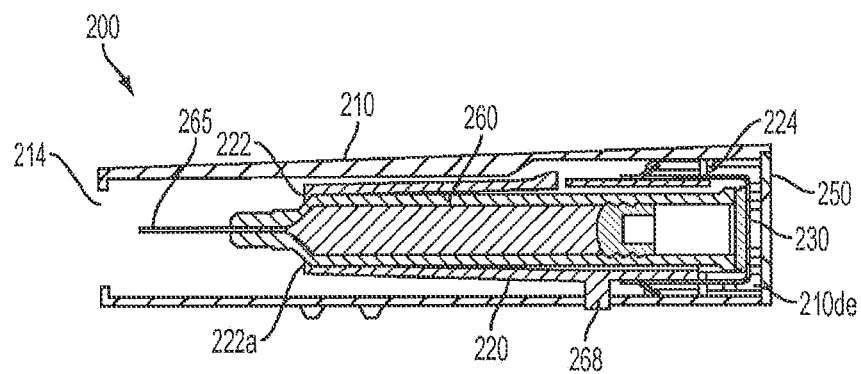
FIG. 5C is a sectional side view of the cassette of FIG. 5A after removal of a cassette cap of the cassette.

Referring collectively to FIGS. 5A-5D, various embodiments of the outer housing 210 of the cassette 200 may comprise a top wall 210*t*, a bottom wall 210*b*, side walls 210*s* connecting the top and bottom walls 210*t* and 210*b*, respectively, a front or proximal end wall 210*pe* and an open rear or distal end 210*de*. The proximal end wall 210*pe* of the outer housing 210 may include an aperture 214 (FIGS. 5C and 5D), which is constructed to removably receive the cassette cap 240. The outer housing 210 may be constructed to retain the inner sleeve 220 therein while allowing it to be freely moved within the outer housing 210 in a slidable manner after removal of the cassette cap 240 (FIG. 5C). Some embodiments of the outer housing 210 may comprise an elongated opening or window 212 in each side wall 210s thereof (FIG. 5A). The outer housing 210 of the cassette 200 may also include a pin 215 (FIG. 5A) or any other suitable mechanical structure that prevents the cassette 200 from being inserted into the cassette door in the wrong direction and/or orientation. An "arrow" icon may be provided on the outer housing 210 (not shown) to indicate the proper direction and orientation for inserting the cassette into the cassette door.

Figure 5D:
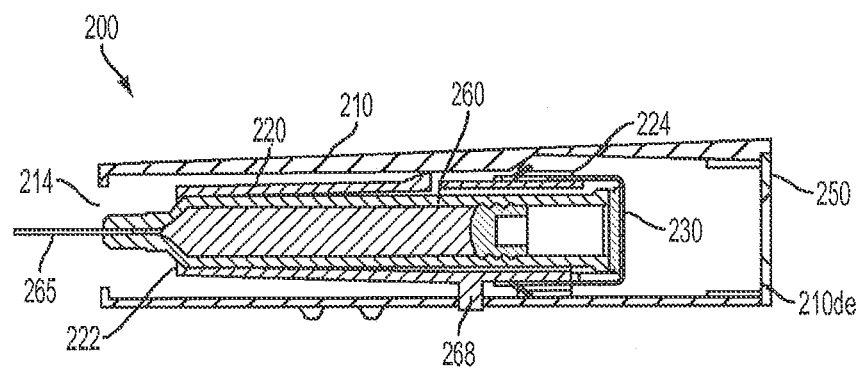
FIG. 5D is a sectional side view of the cassette of FIG. 5C showing a prefilled drug container of the cassette in a needle-injected position.

Referring still to FIGS. 5A-5D, various embodiments of the inner sleeve 220 may comprise proximal and distal ends 222 and 224, respectively. The sleeve 220 may be sized and dimensioned to directly or indirectly hold the drug container 260 therein in a secure manner. The proximal end 222 of the inner sleeve 220 may define an aperture 222a which is constructed to allow the injection needle 265 of the drug container 260 to extend therethrough (FIG. 5C). The inner sleeve 220 may further comprise a drive post 268, which allows it to be driven by the insertion drive of the autoinjector during the needle insertion cycle of the autoinjector's injection cycle. As can be seen in FIGS. 5C and 5D, the inner sleeve 220 can be driven through the outer housing 210 of the cassette 200 by the insertion drive of the autoinjector, during which the drug container 260 moves from a distal position in the outer housing 210 (FIG. 5C) to a proximal position in the outer housing 210 (FIG. 5D) and then back to the distal position. When the inner sleeve 220 is in the distal position (needle-concealed position), as shown in FIG. 5C, the injection needle of the drug container 260 is contained within the outer housing 210 of the cassette 200 and concealed from view by the user. When the inner sleeve 220 is in the proximal position (needle-injection position), as shown in FIG. 5D, the injection needle of the drug container 260 extends out through the aperture 214 in the proximal end wall 210pe the outer housing 210 of the cassette 200 and the autoinjector (not shown). The lock cap 230 closes the open distal end 224 of the inner sleeve 220 thereby locking the drug container 260 within the inner sleeve 220, so that the drug container 260 moves with the inner sleeve 220 as it is driven forward or backward through the outer housing 210 by the insertion drive of the autoinjector, during the insertion cycle of the autoinjector 300. The cover 250 closes the open distal end 210de of the outer housing 210 and prevents tampering with the drug container 260 by encasing the inner sleeve 220 and the drug container 260 within the outer housing 210 of the cassette 200, and also completes the cosmetic appearance of the cassette 200. The inner sleeve 220 may be made from a transparent, rigid material, such as a clear polycarbonate, to allow viewing of the drug container 260 through the windows 212 in the side walls 210s of the outer housing 210.

Figure 6A:
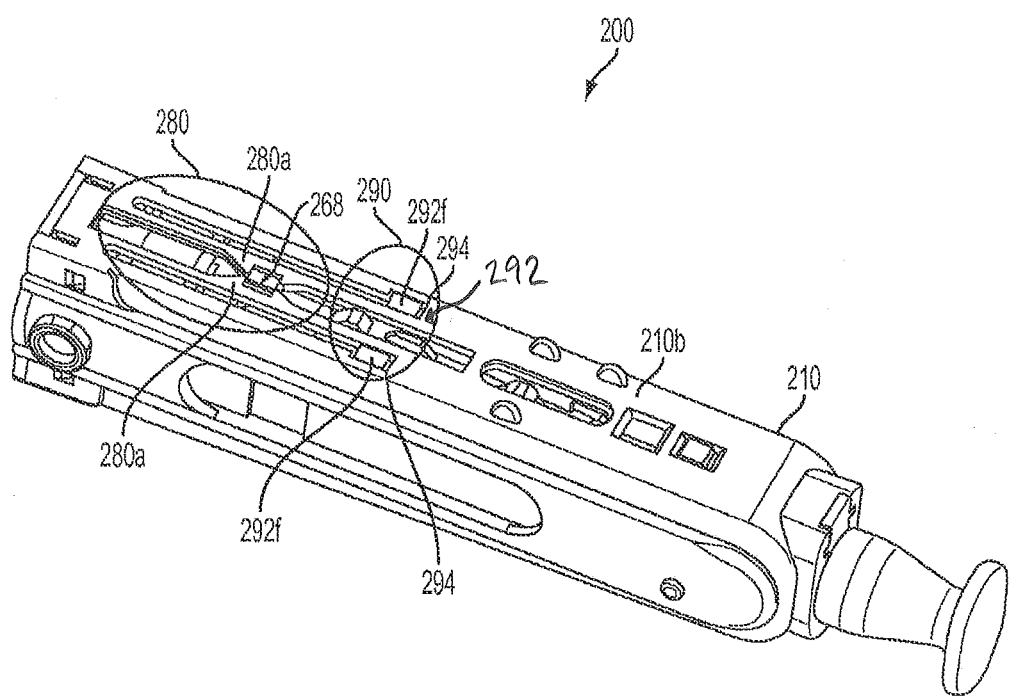
FIG. 6A is a bottom down front perspective view of an embodiment of the cassette showing an inner sleeve latch mechanism and an inner sleeve locking arrangement.
Figure 6B:
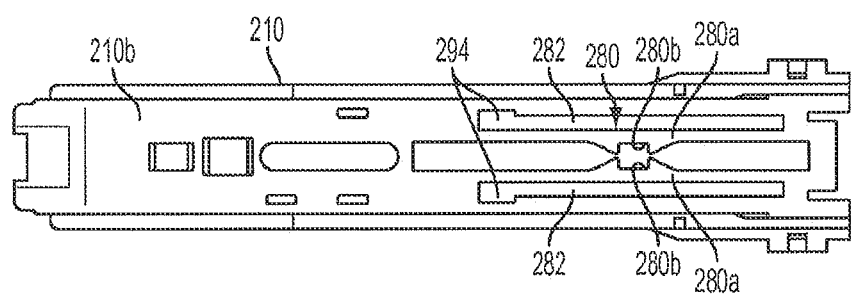
FIG. 6B is a bottom view of an embodiment of an outer housing of the cassette shown in FIG. 6A showing certain elements of the inner sleeve latch mechanism and the inner sleeve locking arrangement.

Referring collectively to FIGS. 6A and 6B, various embodiments of the outer housing 210 of the cassette 200 may comprise a latch mechanism 280 that latches the drive post 268 of the inner sleeve 220 to retain the sleeve 220 and, therefore, the injection needle of the drug container, in a needle-concealed position to protect the drug container and prevent unintentional needle exposure to the user. As best shown in FIG. 6B, the latch mechanism 280 may include a pair of resilient, opposing latch arms 280 a formed in a bottom wall 210b of the outer housing 210, or any other wall of the housing 210 that allows the insertion drive to engage the drive post 268 of the inner sleeve 220. The latch arms 280a may define locking detent slots 280b (FIG. 6B) through which the drive post 268 of the inner sleeve 220 extends.

During assembly of the cassette 200, the inner sleeve 220 containing the drug container, may be inserted into the outer housing 210 so that the drive post 268 of the inner sleeve 220 spreads apart and slides between the latch arms 280a of the outer housing 210 and then enters the detents slots 280b of the latch arms 280a, where it is latched, as shown in FIG. 6A. During the needle-insertion cycle of the autoinjector, the insertion drive moves the distal tab 332d in the proximal direction thereby forcing the latch arms 280a to spread apart and unlatch the drive post 268 of the inner sleeve 220, thereby allowing proximal and distal movement of the unlatched inner sleeve 220 through the cassette outer housing 210, via the drive post 268.

Once unlatched, the insertion drive can move the inner sleeve 220 and, therefore, the drug container disposed therein from the needle-concealed position to the needle injection position. At the completion of the autoinjector's drug-extrusion cycle, the insertion drive moves the drive post 268 and, therefore, the inner sleeve 220 containing the spent drug container back to the needle-concealed position where the drive post 268 is again latched between the latch arms 280a of the latch mechanism 280.

Various other embodiments of the cassette may further comprise an inner sleeve locking arrangement 290, which prevents the inner sleeve 220 from being unintentionally moved within the outer housing 210 from the needle-concealed position. The inner sleeve locking arrangement 290 may replace the latch mechanism 280 or provide redundancy as in the embodiment shown in FIGS. 6A-6B.

The addition of the inner sleeve locking arrangement 290 provides redundancy and increases reliability of the latch mechanism 280, for example, to protect a user from harm, protect the cassette contents, or prevent misuse. The inner sleeve locking arrangement 290 provides improved resistance to motion or locking of the inner sleeve 220 during an impact caused, for example, by a free fall, transportation, and/or handling. Further, the inner sleeve locking arrangement 290 improves impact energy absorption to prevent damage to cassette components. Still further, the inner sleeve locking arrangement 290 provides improved retention of the inner sleeve 220 in the needle-concealed position during removal of the needle shield to prevent exposure of the injection needle to the environment outside the outer housing of the cassette 200. In addition, the inner sleeve locking arrangement 290 more accurately and repeatedly places the inner sleeve 220 in a position for interfacing with the autoinjector.

As shown in FIG. 6B, various embodiments of the inner sleeve locking arrangement 290 may further comprise one or more locking feet receiving slots 294 provided in the bottom wall 210b of the cassette outer housing 210, or any other wall of the housing that interfaces with the cantilever lock arm 292 of the inner sleeve 220. Each of the one or more locking feet receiving slots 294 may be provided at the ends of a pair of elongated slots 282, which define the latch arms 280a of the latch mechanism 280. Each of the locking feet receiving slots 294 is operative for receiving a corresponding one of the locking feet 292f of the cantilever locking arm 292 to effect locking of the inner sleeve locking arrangement 290.

In the above-described embodiments, the inner sleeve locking arrangement provides inner sleeve locking when the cantilever lock arm is in an unbiased state. In various other embodiments, the cantilever lock arm of the inner sleeve locking arrangement can be constructed to provide inner sleeve locking in a biased, actuated position. Such embodiments may be desirable, for example, to hold the inner sleeve and thus, the drug container, in a fixed position at a desired time. In addition, because the motor of the insertion drives the sleeve containing the drug container, the depth of the injection needle can be controlled. This feature can be used in conjunction with the locking feet receiving slots and/or with cassette identification arrangement described further on.

Figure 7A:
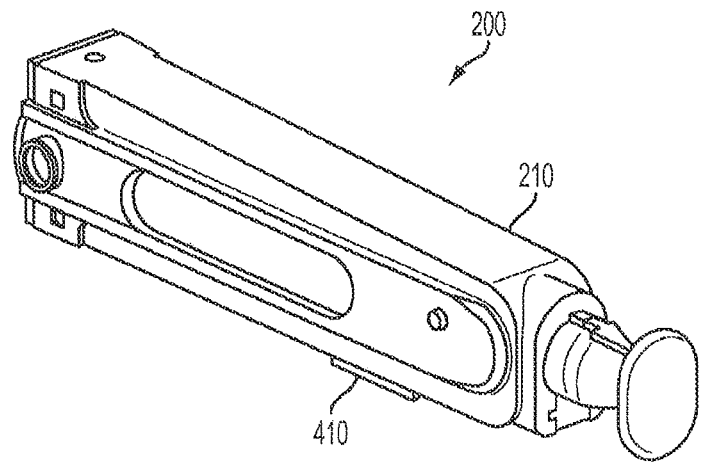
FIGS. 7A and 7B are top down and bottom down front perspective views, respectively, of an embodiment of the cassette with a cassette identification arrangement.
Figure 7B:
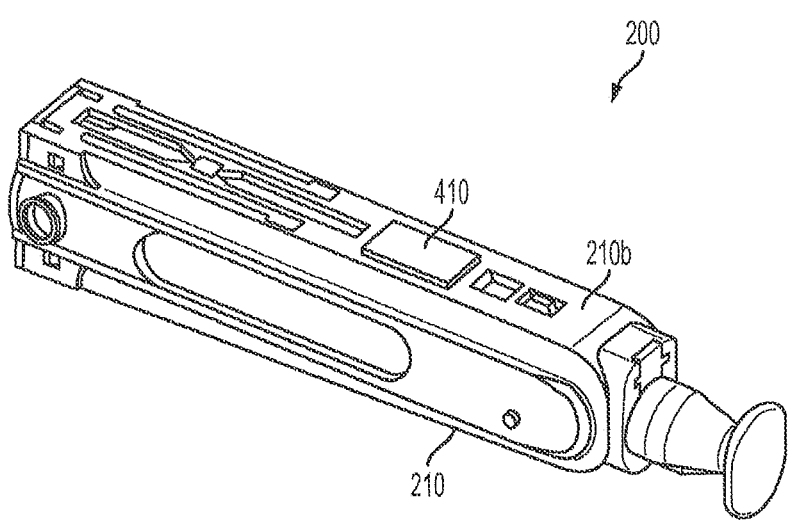

Referring collectively now to FIGS. 7A and 7B, various embodiments of the cassette 200 may further comprise a cassette identification arrangement 410, which may be constructed to communicate information about the cassette 200 to the autoinjector. The cassette identification arrangement 410 may be provided on an exterior surface of the bottom wall 210bs of the cassette outer housing 210 or any other portion of the cassette 200 that is capable of being detected and interpreted by the autoinjector. In some embodiments the information communicated by the cassette identification arrangement 410 may be in the form of a code. Specifically, the cassette identification arrangement 410 may be constructed to generate one of a plurality of different codes, each of which corresponds to certain characteristics of a particular cassette 200. The code allows a suitably adapted autoinjector to determine the type of cassette 200 inserted into the autoinjector, i.e, whether the cassette is a training cassette (i.e., contains no drug receptacle or contains an empty drug receptacle) or a drug cassette containing the drug container prefilled with a drug. Further, the code communicated by the cassette identification arrangement 410 can tell the autoinjector what the drug contained in the drug receptacle is and/or other cassette/drug container characteristics. Still further, the code may provide information that allows the autoinjector to determine, whether the cassette 200 has been inserted into the autoinjector in the proper orientation. The autoinjector can be constructed to automatically select an appropriate operating program and/or adjust its various operational parameters based on the information communicated by the cassette identification arrangement 410 (e.g., with a microprocessor as described earlier). For example, if the autoinjector detects the insertion of a training cassette, the autoinjector can automatically select a training program to train the user on the use of the autoinjector. In another example, if the autoinjector detects the insertion of a drug cassette that contains a drug container prefilled with a certain drug, the autoinjector can automatically select appropriate operating parameters for injecting that drug, such as injection speed, needle insertion speed, pre and post-injection wait time, needle insertion depth, temperature limits, etc. Available speed ranges may be dependent upon the drug container fill volume and drug characteristics, such as viscosity. Automatic selection by the autoinjector of its operating parameters eliminates the need for the user to have to determine the appropriate operating parameters for a given drug and then manually input them into the autoinjector.

Figure 8A:
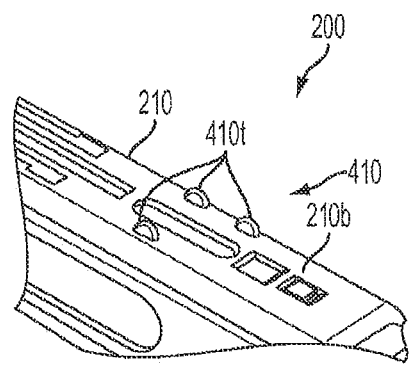
FIG. 8A is a bottom down perspective view of a portion of the cassette showing an embodiment of the cassette identification arrangement.
Figure 8B:
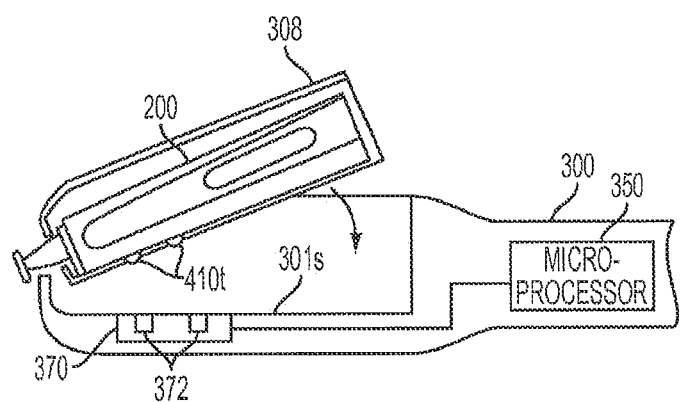
FIG. 8B is a sectional side view of the cassette of FIG. 8A being inserted into an autoinjector constructed to detect and decipher the cassette identification arrangement embodied in FIG. 8A.

As shown in FIG. 8A, various embodiments of the cassette identification arrangement 410 may comprise one or more projections or tabs 410t provided on or in the bottom wall 210b of the cassette outer housing 210. The number and location of the tabs 410t may define the code or at least a portion of the code, which represents information about the cassette 200. As shown in FIG. 8B, the cassette identification arrangement 410 may further comprise a detector 370 that may be provided on or in the cassette support surface 301s of the autoinjector 300 to sense the number and location of the tabs 410t when the cassette 200 engages the cassette support surface 301s as the autoinjector door 308 is closed. The detector 370 may be communicatively coupled to a microprocessor 350 contained within the autoinjector 300, thereby enabling the autoinjector 300 to detect the tabs 410t and obtain the code representing the information about the cassette 200. In various embodiments, the detector 370 may comprise a plurality of conventional, flat-flush mounted, momentary, push-button switches 372. The switches 372 may be arranged to engage corresponding ones of the tabs 410t. None, some, or all of the switches 372 may be actuated by the tabs 410t of the cassette 200, depending upon the arrangement of tabs 410t and the code they represent, when the cassette 200 is supported on the cassette support surface 301s of the autoinjector 300. Therefore, the code defined by the tabs 410t and the information that the code represents about the cassette 200 can be communicated to the microprocessor 350 of the autoinjector 300 for deciphering.

The tabs 410t can be differentiated from each other by their individual location on or in the cassette housing 210. By utilizing the presence or absence of tabs 410t, multiple combination codes can be created such that each code identifies a particular cassette 200 or characteristics of the cassette. Although the cassette identification arrangement 410 shown in the embodiment of FIG. 8A comprises three tabs 410t, various other embodiments of the cassette identification arrangement 410 may comprise more or less than three tabs in order to increase or decrease the number of programming codes available. In the embodiment shown in FIG. 8A, the presence and/or absence of one or more of the three tabs 410t provides up to eight (8) different possible cassette identification codes, which can be detected and deciphered by the autoinjector 300. As mentioned earlier, the information represented by each code can be used to define one of a plurality of programming instructions for the autoinjector 300 and/or to communicate secondary information to the autoinjector 300, such as, but not limited to, verifying that the cassette 200 is an authorized OEM device, and/or verifying the proper insertion of the cassette 200 into the autoinjector 300.

Various other embodiments of the tabs 410t of the cassette identification arrangement 410 may have different heights. In such embodiments, the autoinjector's push-button switches 372 and microprocessor 350 can be constructed to allow them to differentiate between tabs 410t of the different heights, for example, but not limitation, by how far in a button (not shown) of the push-button switch 372 is depressed into the switch 370 by the tab 410t. Embodiments comprising both short and tall tabs 410t can provide each possible tab location on the cassette outer housing 210 with one of three possible states, e.g.:

State 1: no tab present
State 2: short tab present
State 3: tall tab present

If the cassette identification arrangement 410 comprises, for example, up to three tabs 410t where each such tab 410t is short or tall, the autoinjector could detect up to twenty-seven (27) different tab states to increase the number of possible codes.

Figure 9A:
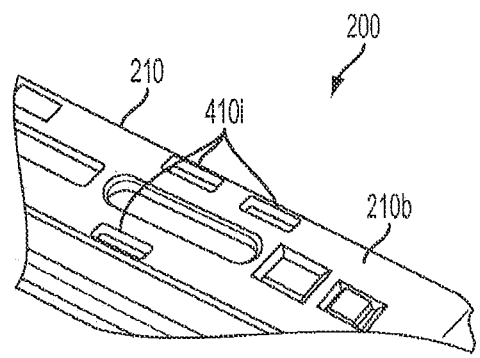
FIG. 9A is a bottom down perspective view of a portion of the cassette showing another embodiment of the cassette identification arrangement.
Figure 9B:
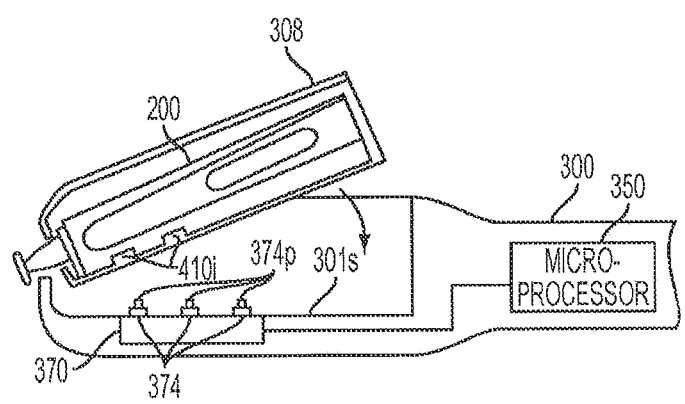
FIG. 9B is a sectional side view of the cassette of FIG. 9A being inserted into an autoinjector constructed to detect and decipher the cassette identification arrangement embodied in FIG. 9A.

As shown in FIG. 9A various other embodiments of the cassette identification arrangement 410 may comprise one or more indentations 410i provided in the bottom wall 210b of the outer housing 210 of the cassette 200. As shown in FIG. 9B, in such embodiments of the cassette identification arrangement 410, the detector 370 of the autoinjector 300 may comprise a plurality of conventional pogo-pin switches 374n to detect the presence or absence of the indentations

410*i*. The coding, detection, deciphering, and parameter control functions are generally the same as described above with respect to the tabs 410*t*.

Various other embodiments of the indentations 410*i* of the cassette identification arrangement 410 can have different depths. In such embodiments, the autoinjector's pogo-pin switches 374 and microprocessor 350 can be constructed to allow them to differentiate between indentations of the different depths by how far in a pin 374*p* of the pogo-pin switch 374 is depressed into the switch by the indentation, to increase the number of possible different codes.

In various further embodiments, the cassette identification arrangement 410 of the cassette may comprise a combination of the above-described tabs 410*t* and indentations 410*i*. The autoinjector, in such embodiments may then be constructed to include corresponding push-button and pogo-pin switches 372, 374.

The codes defined by the tabs 410*t* and/or indentations 410*t* of the cassette identification arrangement 410 communicate information about the cassette 200 to the autoinjector 300, which can then use this information to automatically adjust its programming, etc. For example, but not limitation, one tab 410*t* or indentation 410*i* may define a code that indicates that the cassette 200 contains a drug container filled with 1 mL of a drug and two tabs 410*t* or indentations 410*i* may define a code that indicates that the cassette 200 contains a drug container filled with 0.5 mL of a drug. An additional tab 410*t* or indentation 410*i* in the same cassette identification arrangement may provide a code that identifies the drug and/or characteristics of the drug. In another example, the code for a training cassette may comprise the presence of all the possible tabs 410*t* and/or indentations 410*i*. In a further example, the absence of one of the tabs 410*t* and/or indentations 410*i* may define a code for a certain drug. Different combinations of tabs 410*t* and/or indentations 410*i* can be used to differentiate between different drugs or to indicate the absence of the drug container, for the purpose of controlling the autoinjector parameters.

Figure 10A:
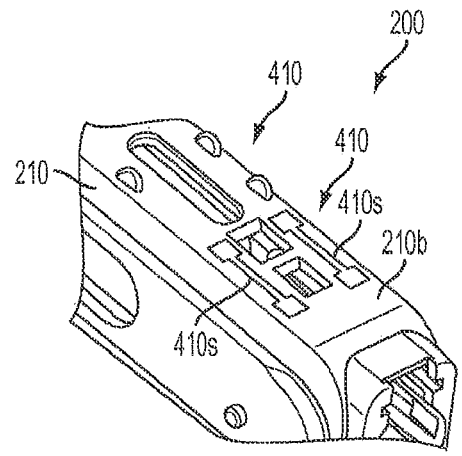
FIG. 10A is a bottom down front perspective view of a portion of the cassette showing another embodiment of the cassette identification arrangement.
Figure 10B:
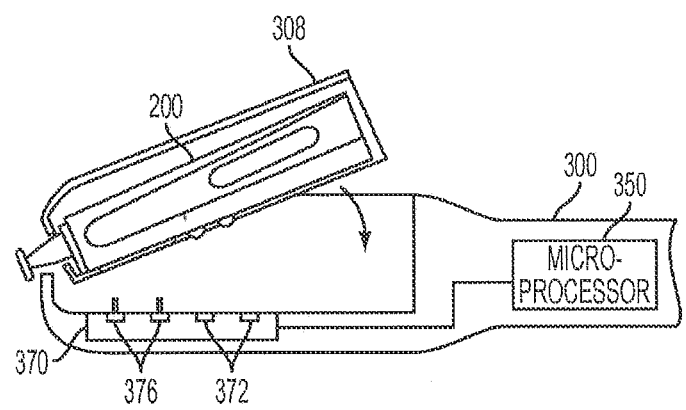
FIG. 10B is a sectional side view of the cassette of FIG. 10A being inserted into an autoinjector constructed to detect and decipher the cassette identification arrangement embodied in FIG. 10A.

As shown in FIG. 10A, various other embodiments of the cassette identification arrangement 410 may comprise one or more flat, electrically conductive traces or strips 410*s* provided on the outer surface of the bottom wall 210*b* of the outer housing 210. In such embodiments of the cassette identification arrangement 410, as shown in FIG. 10B, the detector 370 of the autoinjector 300 can be constructed with pogo-pin connectors 376 that contact the conductive strips 410*s* when the cassette 200 is inserted into the autoinjector 300. The conductive strips 410*s* can be molded into the exterior surface of the cassette's bottom wall 210*b*, screen-printed onto that surface, or comprise a separate component, such as a flex-cable material, affixed to that surface with pressure sensitive adhesive or any other suitable means.

In various embodiments, the one or more conductive strips 410*s* can be operative as a cassette presence sensor, where each of the conductive strip 410*s* may operate to close an electrical circuit of the detector 370 between two pogo-pin connectors 376 when the cassette 200 is mounted on the support surface 301*s* of the autoinjector 300. In some embodiments, the conductive strips 410*s* can be constructed to form a straight path (e.g., as show in FIG. 10A) to connect inline arranged pogo-pin connectors, or constructed to form a tortuous path to connect pogo-pin connectors that require jagged or tortuous path to connect. In other embodiments, the conductive strips 410*s* can be constructed to have a specific electrical resistance, capacitance, inductance, etc., which would define a code capable of detection via the electrical circuit of the detector 370, which in turn would communicate the code and, therefore, the associated cassette information to the microprocessor 350 of autoinjector 300, such as drug, fill volume, injection speed, etc.

As further shown in FIGS. 10A and 10B, various embodiments of the cassette identification arrangement 410 may combine the one or more conductive strips 410*s* with the one or more tabs 410*t* (and/or indentions 410*i*) described earlier. In such embodiments of the cassette identification arrangement 410, the detector 370 and microprocessor 350 of the autoinjector 300 can be constructed to have the appropriate push-button switches 372 and pogo-pin switches 374 (and/or pogo-pin connectors 376). It should be understood, however, that the cassette identification arrangement 410 may only comprise the one or more conductive strips 410*s*.

Figure 11A:
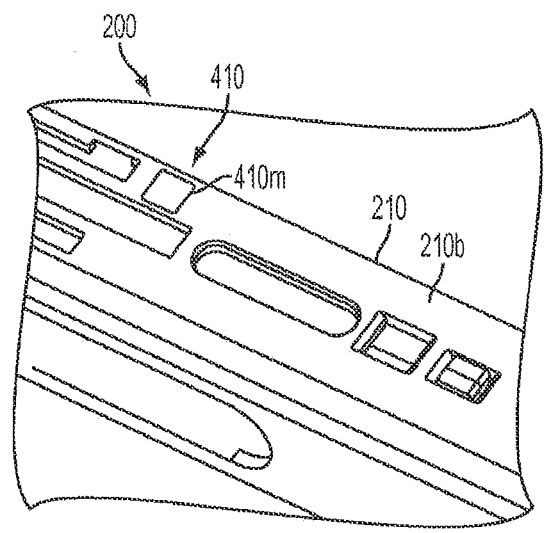
FIG. 11A is a bottom down perspective view of a portion of the cassette showing a further embodiment of the cassette identification arrangement.

As shown in FIG. 11A, various other embodiments of the cassette identification arrangement 410 may comprise one or more magnets 410*m* embedded in the bottom wall 210*b* of the cassette outer housing 210 or provided on the exterior or interior surface of the bottom wall 210*b* of the cassette outer housing 210. In such embodiments of the cassette identification arrangement 410, the detector 370 of the autoinjector 300 (e.g., FIGS. 8B-10B) can be constructed as a Magnetic Resonance (MR) sensor or other magnetic-sensing sensor that is activated by the one or more magnets when the cassette 200 is inserted into the autoinjector 300. The one or more magnets 410*m* should be of sufficient strength to activate the MR sensor. The magnet and MR sensor arrangement can be used alone or combined with any of the other previously described cassette identification arrangements 410.

Figure 11B:
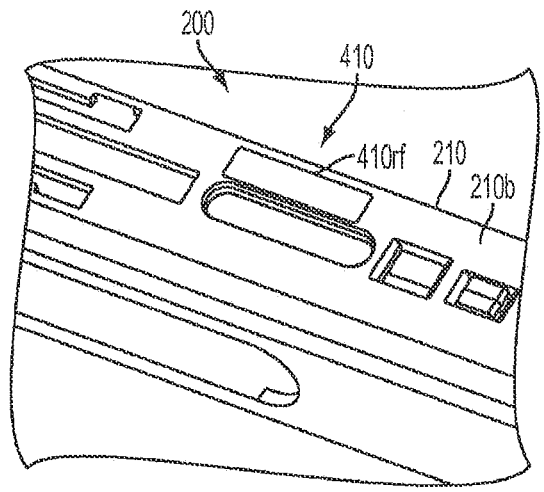
FIG. 11B is a bottom down perspective view of a portion of the cassette showing still another embodiment of the cassette identification arrangement.

As shown in FIG. 11B, various further embodiments of the cassette identification arrangement 410 may comprise a radio-frequency (RF) electromagnetic field (EMF) emitting device 410*rf*, such as RF identification (RFID) chip. The detector 370 of the autoinjector 300 (e.g., FIGS. 8B-10B) can be constructed as an EMF receiving device, such as an RFID chip reader, that is activated by the RF EMF device 410*rf* when the cassette 200 is inserted into the autoinjector 300. The RF EMF device 410*rf* can be molded into or attached to the bottom wall 210*b* of cassette outer housing 210 or any other suitable portion of the cassette 200 that allows the RF EMF device 410*rf* to communicate with the detector 370 of the autoinjector 300.

Figure 11C:
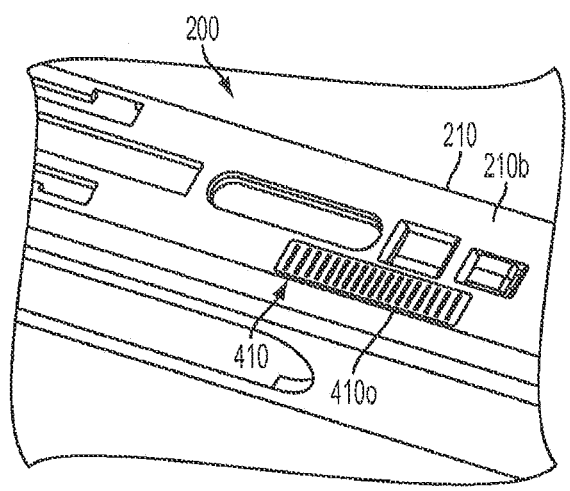
FIG. 11C is a bottom down perspective view of a portion of the cassette showing yet another embodiment of the cassette identification arrangement.

As shown in FIG. 11C, various other embodiments of the cassette identification arrangement 410 may comprise one or more optical machine-readable (OMR) identifiers 410O. The one or more OMR identifiers 410*o* may comprise, without limitation, one or more bar-code labels, one or more color-coded labels, one or more other suitable OMR identifiers, or any combination thereof. OMR identifiers 410*o* embodied as bar-code labels may comprise, but are not limited to, 1-dimensional and 2-dimensional matrix codes. The detector 370 of the autoinjector 300 (e.g., FIGS. 8B-10B), in such embodiments, can be constructed as an optical scanner. The OMR identifier 410*o* may be provided on the exterior surface of the bottom wall 210*b* of the cassette's outer housing 210 or any other suitable portion or area of the cassette 200 that is capable of interfacing with the detector 370 of the autoinjector 300.

The RF EMF device 410*rf* and one or more OMR identifier labels 410*o* can be applied to the cassette before or after it is assembled with the prefilled drug container. This allows the RF EMF device 410*rf* and/or one or more OMR identifier labels 410*o* to include additional information or programming, such as the date of manufacture, location of manufacture, expiration date of drug, drug temperature stabilization time in order to allow the drug to reach an optimal temperature prior to injection), and autoinjector verification that the cassette 200 and drug are OEM components.

Figure 11D:
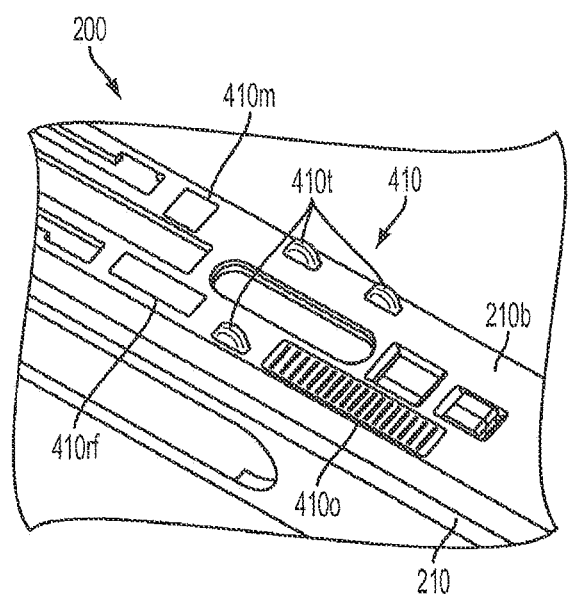
FIG. 11D is a bottom down perspective view of a portion of the cassette showing another embodiment of the cassette identification arrangement.

As shown in FIG. 11D, various other embodiments of the cassette identification arrangement 410 may comprise the one or more magnets 410m, the RF EMF emitter device 410rf, the one or more OMR identifiers 410o and the tabs 410t (and/or indentations 410i) described earlier, each defining a portion of the code provided by the arrangement 410. In such embodiments of the cassette identification arrangement, the detector 370 of the autoinjector can be constructed with the appropriate switches, sensors, receivers, and/or scanners (e.g., FIGS. 8B-10B) to detect the corresponding cassette elements of the cassette identification arrangement 410.

Figure 12:
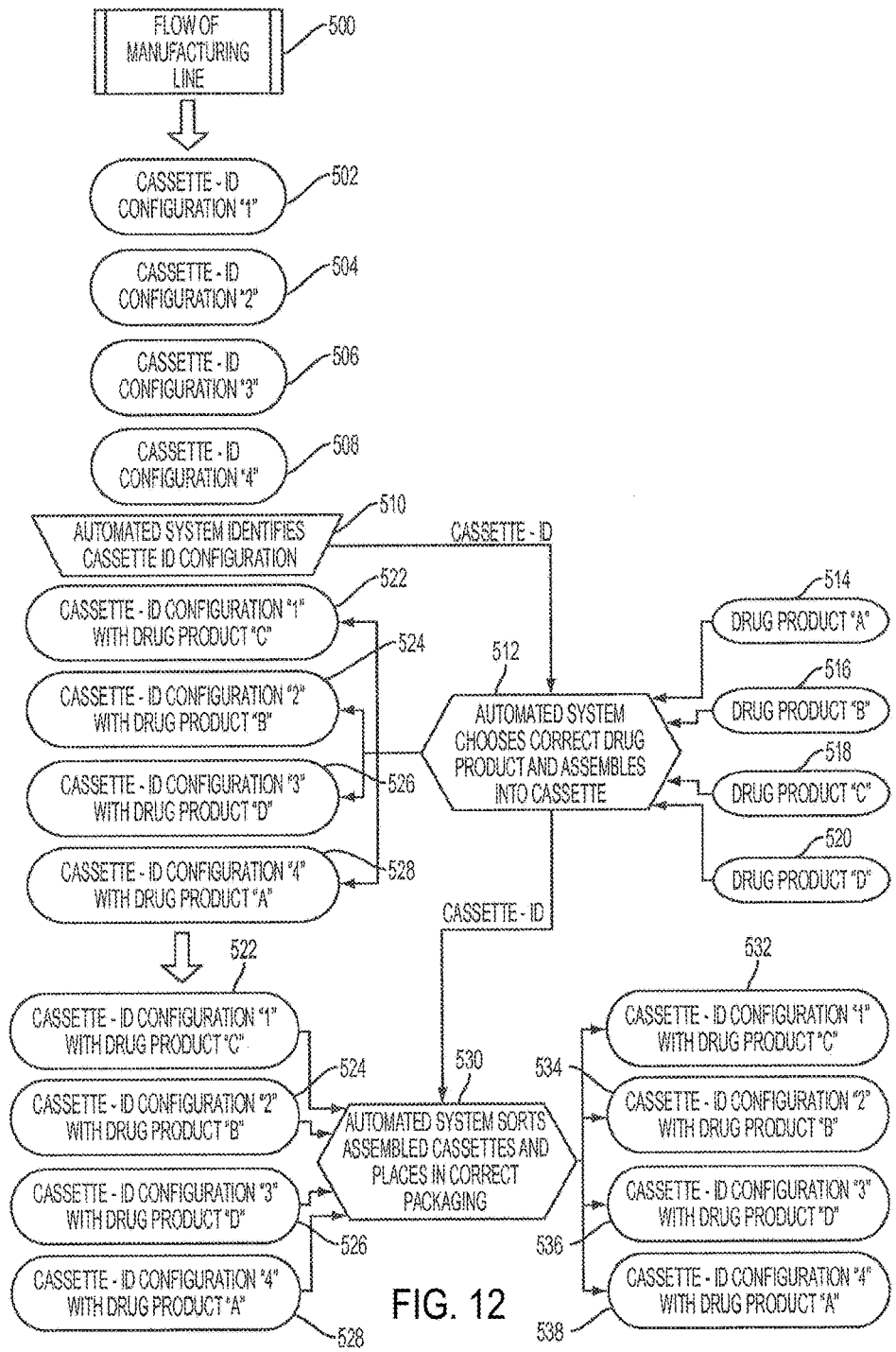
FIG. 12 is a flow chart showing an embodiment of a method for assembling different product lines on a single manufacturing line using the cassette identification arrangement to control the assembly of prefilled drug containers (containing a range of different drugs and/or fill levels) and to rout the assembled cassettes to the appropriate packaging stations.

The cassette identification arrangement 410 may also be used to control aspects of the cassette manufacturing and packaging processes. FIG. 12 shows a flow chart which shows an example of how a single production or manufacturing line may be used to assemble different product lines using the cassette identification arrangement to control the assembly of the prefilled drug containers (containing a range of different drugs and/or fill levels) and then rout the assembled cassettes to the appropriate packaging stations. Block 500 represents a single manufacturing line which may comprise a computer controlled manufacturing system and blocks 502, 504, 506, and 508 may represent four unassembled cassettes in the line each having its own cassette identification arrangement configuration (1, 2, 3, or 4) of tabs, indentations, etc. Each of the unassembled cassettes 502, 504, 506, and 508 are to be assembled with a drug container having one of four different drugs (A, B, C, or D) that matches the cassette identification arrangement configuration (cassette ID configuration). In the embodiment shown in FIG. 12, the manufacturing system may be programmed such that cassette ID configuration 1 identifies drug C, cassette ID configuration 2 identifies drug B, cassette ID configuration 3 identifies drug D, and cassette ID configuration identifies drug A.

In block 510, the manufacturing system of the line identifies the cassette ID configuration of each of the unassembled cassettes 502, 504, 506, and 508. For each of the unassembled cassettes 502, 504, 506, and 508, the system in block 512 selects a matching one of the drug containers 514, 516, 518, and 518 prefilled with drugs A, B, C, and D, respectively, using the identified cassette ID and assembles it with the unassembled cassette 502, 504, 506, and 508. Therefore, in block 512, unassembled cassette 502 with cassette ID configuration 1 may be assembled with drug container 518 prefilled with drug C to generate assembled cassette 522, unassembled cassette 504 with cassette ID configuration 2 may be assembled with drug container 516 prefilled with drug B to generate assembled cassette 524, unassembled cassette 506 with cassette ID configuration 3 may be assembled with drug container 520 prefilled with drug D to generate assembled cassette 526, and unassembled cassette 508 with cassette ID configuration 4 may be assembled with drug container 514 prefilled with drug A to generate assembled cassette 528.

In block 530, the manufacturing system sorts assembled cassettes 522, 524, 526, and 528 using their cassette ID configurations 1, 2, 3, and 4, respectively, and places them in packages 532, 534, 536, and 538 for drugs C, B, D, and A, respectively.

Figure 13:
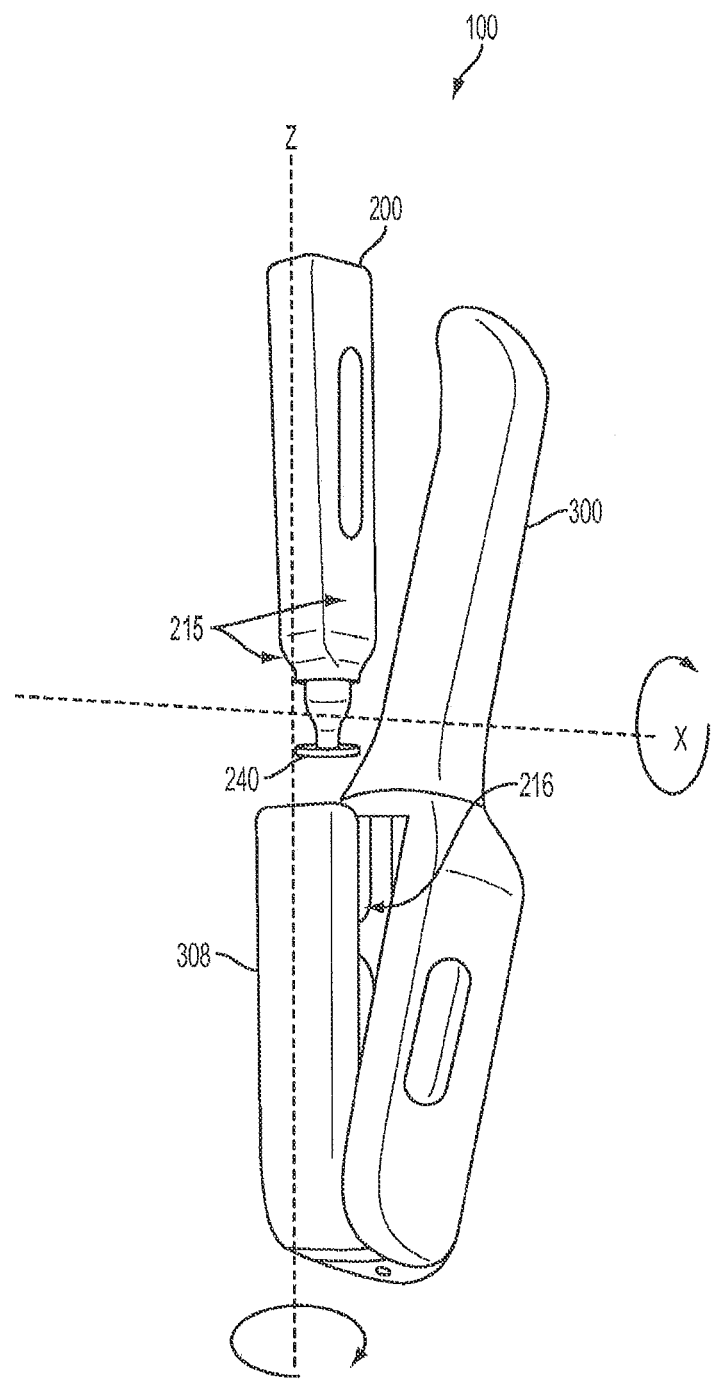
FIG. 13 is a bottom up perspective view of the autoinjector of the autoinjector apparatus or system showing the installation of a cassette into the autoinjector.

Referring now to FIG. 13, the autoinjector system 100 may be constructed to force users to execute the steps of the injection process in a safe and reliable order, which simplifies the operation of the autoinjector system 100. By controlling the sequence of actions performed by the user, the injection process can be made more reliable. Accordingly, in various embodiments, the autoinjector system 100 is constructed to force or cause the user to perform the following steps in sequence: inserting the cassette 200 into the autoinjector 300; preparing the autoinjector system 100 for injection; placing the autoinjector 300 on skin and starting the injection process; and disposing of the used cassette 200 and storing the autoinjector 300 for future use. Performing these steps in sequence ensures autoinjector system reliability and user safety.

As described above, various embodiments of the autoinjector 300 and cassette 200 can comprise mechanical, electromechanical, and other structures that provide feedback signals to the microprocessor (not shown) of the autoinjector 300. The microprocessor may be programmed with instructions (e.g., algorithm), which when executed thereby, allow these signals to be evaluated by the microprocessor in order to enable the autoinjector 300 to move through discrete logic "states" where the autoinjector system 100 is in a known configuration.

Figure 14:
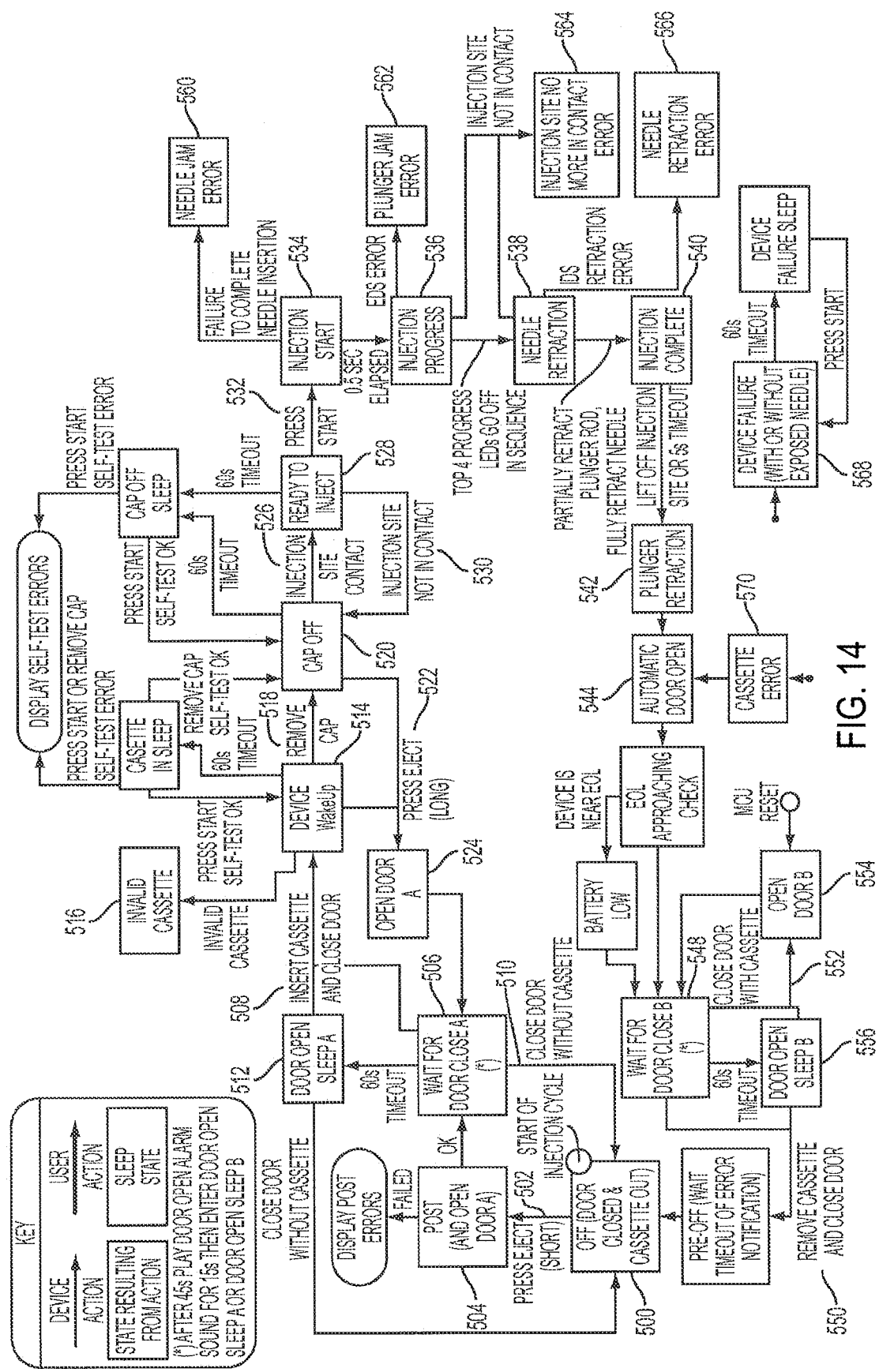
FIG. 14 is a flow chart showing an embodiment of the decision logic for forcing a user to execute the steps of an injection process in a safe and reliable order.

Referring now to FIG. 13 in conjunction with the flow chart of FIG. 14, an embodiment of the decision logic for controlling the various functions of the autoinjector system 100, will be described. The decision logic forces the user to perform, in sequence, the steps of: inserting the cassette 200 into the autoinjector 300; preparing the autoinjector system 100 for injection; placing the autoinjector 300 on skin and starting the injection process; and disposing of the used cassette 200 and storing the autoinjector 300 for future use.

Insertion of the Cassette into the Autoinjector

In block 500 (Off, Door Close, Cassette Out), prior to use, the autoinjector system 100 may be in a state where the only button that is active is the one to initiate cassette door opening (eject button) and all other buttons are deactivated. This may force the autoinjector system 100 only to respond to a single user action of pressing the eject button at arrow 502 and all other actions may be ignored or may not be possible. Once the cassette door 308 of the autoinjector 300 opens in block 504, the user may insert the cassette 200 into the door. In various embodiments, the autoinjector 300 and cassette 200 may comprise certain structures that allow the insertion of the cassette 200 only in the correct orientation, such as one or more pins 215 on the cassette 200, which interacts with a corresponding slot or pin 216 in the cassette door 308 of the autoinjector 300, as shown in FIG. 14, to allow insertion only in the correct orientation and prevent insertion in orientations about the insertion axis (z axis). The cassette 200 may also have a tapered shape or other structure, which matches with the cassette door 308 of the autoinjector 300 to prevent rotation about the x axis.

While waiting for the user to insert the cassette 200, the autoinjector 300 may transition to a known state in block 506 (Wait for Door Close A) where all other actions from the user with the exception of closing the door may be ignored such as pressing of start and eject buttons, etc.

This may force the user to either close the cassette door 308 with a cassette 200 at arrow 508 to proceed with the injection process, or close the door at arrow 510 without a cassette 200 as the autoinjector system 100 moves to the previous known state of block 500. If the user chooses not to perform the required action, the autoinjector system 100 continues to remain in the same state in block 512 (Door Open).

If the user inserts a cassette 200 of either an unknown configuration and/or a used cassette 200 into the cassette door 308 and closes at arrow 508, the autoinjector system 100 detects this state using, for example the cassette identification arrangement described earlier, and does not allow the process to continue to the next state in block 516. Accordingly, the user is forced to insert a valid cassette 200 (known configuration and unused) in the correct orientation into the autoinjector 300 in order to proceed.

Preparing the Autoinjector System for Injection

Once the cassette door 308 of the autoinjector 300 has been closed with a valid cassette 200, the autoinjector system 100 may move to an active state in block 514 (Device Wakeup). The next step by the user in this configuration is to remove the cassette cap 240 at arrow 518. As described above, the autoinjector system 100, in various embodiments, may be capable of detecting the presence or absence of the cassette cap 240, and may also capable of monitoring a transition in the state of a cassette cap remover switch that may be provided in the autoinjector 300 from presence to absence. This transition may be used by the autoinjector system 100 to detect the removal of the cassette cap 240 by the user and moving the autoinjector system 100 to the state of block 520 (Cap Off). This may force the user to either remove the cassette cap 240 at arrow 518 to proceed with the injection process, or abort the process by pressing the eject button at arrow 522, which opens the door at block 524 (Open Door A) to allow the cassette 200 to be removed and returns the autoinjector system 100 to the last known state at block 506 (Wait for Door Close A). If the user chooses not to perform the required actions, the autoinjector system 100 continues to remains in the same state at block 515 (Cassette in Sleep).

To ensure that these actions are truly intended by the user and not accidentally initiated, the cassette cap removal and abort process may require a committed action. Cassette cap removal may have a minimum pull off force and pull off direction such that a user or patient needs to purposefully hold and pull off the cassette cap in order to remove the needle shield. In other words, there is minimum removal force and direction for removal (pulling straight down) such that the cassette cap cannot be accidentally removed by normal handling. For the abort process, this may be achieved by requiring the user to press and hold the eject button for a set time period at arrow 522 before the eject process is initiated.

Place on Skin and Start the Injection Process

With a valid cassette 200 inserted into the autoinjector 300, the cassette cap 240 removed, and the autoinjector system 100 in the state of block 520 (Cap Off), the user may place the autoinjector 300 on the injection site (skin) at arrow 526. As described above, various embodiments of the autoinjector 300 may include a skin sensor to allow the autoinjector system 100 to detect proximity to the injection site. Therefore, the autoinjector system 100 can allow the user to proceed with the injection process only when the injection site is detected. As described above, the microprocessor may be programmed with instructions, which allow the injection site presence to be indicated only when it detects a continuous positive signal from the skin sensor. This ensures that the user is committed to the process and has a stable contact with the injection site in order to move to the state of block 534 (Ready to Inject). As described above, various embodiments of the cassette cap 240 may have a structure that does not allow it to be reinserted into the cassette 200 once removed, thereby preventing the user from reinserting the cassette cap 240 and moving back to the prior state of block 514 (Device Wakeup).

This forces the user to either hold the autoinjector 300 with a stable contact at the injection site in order to proceed with the injection process at block 534 or abort the process by pressing the eject button at arrow 522, which opens the door at block 524 to allow cassette removal and returns the autoinjector system 100 to the last known state after door opening at block 506 (Wait for Door Close A). If no stable signal is obtained at arrow 530, the autoinjector system 100 may continue to remain in the state of block 520 (Cap Off). If injection site contact is lost at any point in time, the autoinjector system 100 may return to the state of block 520 (Cap Off).

Once the above conditions are met and the autoinjector system 100 is in the state of block 526 (Ready to Inject), the user in this configuration activates the injection at arrow 532. Once initiated, the autoinjector system 100 may reconfirm the cassette identification arrangement, skin sensor and the like, to confirm its expected configuration and once confirmed, it may automatically execute in sequence, needle injection and drug extrusion in block 536 (Injection Progress), (Needle Retraction) in block 538, (Injection Complete) in block 540, (Plunger Retraction) in block 542 and (Automatic Door Open) in block 544, to allow for cassette removal and disposal at block 548 (Wait for Door Close B). Immediately after injection initiation by the user, all other buttons and switches on the autoinjector 300 may be disabled to prevent unintentional activation of the buttons by the user during the injection process.

During the injection process, the autoinjector system 100 constantly continuously monitors the status of the injection site contact in block 564. The process may be terminated if at any point in time there is a loss in injection site contact for a predetermined time (e.g., the user intentionally removes the autoinjector 300 from the injection site or adjusts the position in such a way that a reliable delivery process cannot be ensured). In addition, autoinjector system 100 may check for various mechanical errors during the injection process in block 560 (Needle Jam Error), block 562 (Plunger Jam Error), block 566 (Needle Retraction Error), block 568 (Device Failure), and block 570 (Cassette Error).

If desired, the microprocessor 350 of the autoinjector 300 may be programmed with instructions that, when executed by the microprocessor 350, enable the autoinjector to control and monitor the insertion drive 330 to insert the needle 265 at two sequential speeds. More specifically, the microprocessor 350 can insert the needle 265 at a first, higher speed to begin the insertion process, a second, lower speed to finish the insertion process, with the momentum of the needle 265 and components thereof carrying the needle 265 to a final stop. In one example, the first speed is about 0.4 m/s and the second speed is about 0.2 m/s.

Monitor the Progress of the Injection Process

An autoinjector drug delivery device 300 configured with a stall and endpoint detection algorithm is described herein that allows for variations in the fill of the drug 267, the syringe or barrel 261, plunger 264, and other components of the autoinjector 300 as set forth above. The algorithm is effective over a range of situations, configurations, and conditions. A stall or end point detected by the algorithm during an injection leads the microprocessor 350 to stop the injection process, retract the plunger rod 342, and remove the needle 265 from the injection site.

The microprocessor 350 of the autoinjector 300 operates software that tracks the position of the plunger rod 342, such as by counting signals from the rotary encoder 342 with the optical sensor 352. The count begins at zero and has an expected end count, e.g., 2500 counts. The software samples the absolute position of the plunger rod 342 at set intervals, e.g., 5 mS. Utilizing counts and timing, the algorithm can determine whether the plunger rod 342 is simply slowing or temporarily stalling vs. stopping or reaching the end of the barrel 261. Further, the microprocessor 350 can compare readings to past samples and the algorithm can be configured to utilize the past samples, which can provide an expected end point, to determine when to stop the injection, retract the plunger rod 342, remove the needle 265, and end the injection process.

Figure 15:
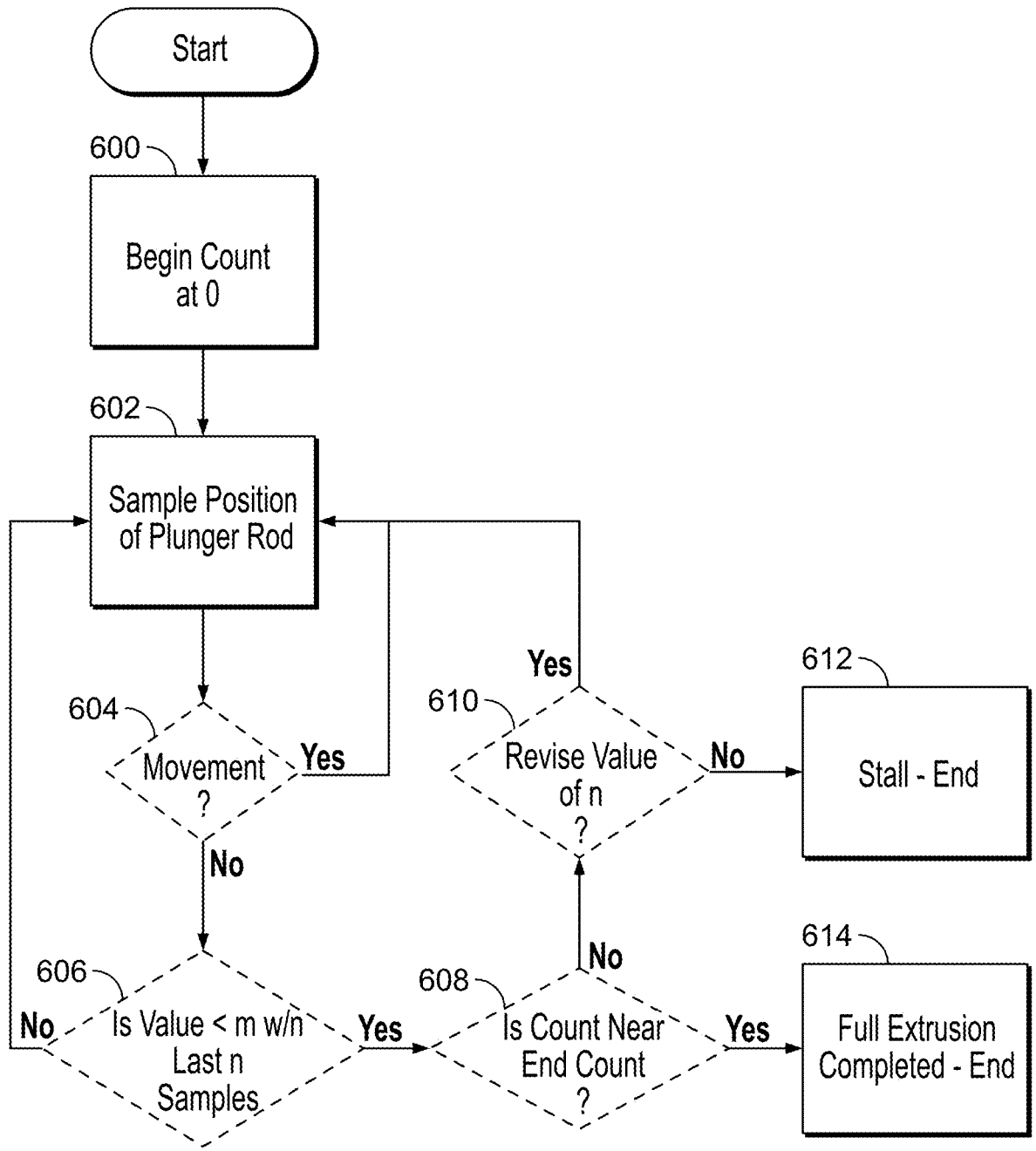
FIG. 15 is a flow chart showing an end point and stall detection algorithm.

A flowchart for such an algorithm is shown in FIG. 15. Generally, the microprocessor 350 follows the logic of the algorithm to sample counts of the signals from the encoder 346 to determine the position of the plunger rod 342 and, therefore, the plunger 264 during the injection process. By setting the values of the sample intervals, a number of counts indicating movement, and associations therebetween, the algorithm allows the microprocessor 350 to determine whether the plunger as stalled or reached an expected end point.

At block 600, the drug extrusion process starts and the algorithm begins at count 0. After a predetermined interval has passed (e.g., 5 mS), in block 602 the algorithm takes a sample of the injection position based on counts of the rotary encoder 346 with the optical sensor 352. In block 604, the algorithm determines if the sample indicates movement of the plunger rod 342. If there is movement, the algorithm returns to block 602 to take another sample of the position of the plunger rod. If there is no movement, then in block 606, the algorithm determines if there has been movement less than a count of m signals detected by the encoder 346 has been detected within the last n number of samples. If no, the algorithm loops back to block 602 and the plunger position is re-sampled. Alternatively, if total movement is less than m within last n samples, then in block 608, the algorithm compares the total count number to an expected end count x. If the total count number is not near to or is less than the end count x, the algorithm determines that the injection is incomplete and proceeds to block 610. In block 610, if the end count is not near, then 'value <m within last n samples' can be rechecked with different values m and n. This is to check for stalls during extrusion due to the variations and conditions set forth above. If a stall is detected during extrusion, the motor is stopped, and the algorithm ends in block 612, Otherwise, the algorithm continues back to block 602 to re-samples plunger position. Back to block 608, if the total count number is near to or is greater than the end count x, the algorithm moves to block 614, and determines that a full dose of the drug 267 has been dispensed.

With this configuration, selection of the value of n determines the sensitivity of the speed at which a stall is detected. For example, if a stall can be detected between [n and (n+1)] samples without movement detected, then a stall in an injection process having a duration between [(n*5 mS) and ((n+1)*5 mS)] can be detected. The range of speeds (counts per second) at which the plunger is moving when a stall is detected is given by [(1000*m)/((n+1)*5 mS) and (1000*m)/((n)*5 mS)] where 1000 is the conversion factor 1000 mS/S and 5 mS is the sampling rate.

TABLE 1

| Stall Detection Ranges for m = 1 | | | |
|---|---|---|---|
| n | Stall detection time range [mS] | | Stall detection speed range [cnt/sec] |
| 10 | 50 | 55 | 18.2 20.0 |
| 9 | 45 | 50 | 20.0 22.2 |
| 8 | 40 | 45 | 22.2 25.0 |
| 7 | 35 | 40 | 25.0 28.6 |
| 6 | 30 | 35 | 28.6 33.3 |
| 5 | 25 | 30 | 33.3 40.0 |
| 4 | 20 | 25 | 40.0 50.0 |
| 3 | 15 | 20 | 50.0 66.7 |
| 2 | 10 | 15 | 66.7 100.0 |

Figure 16:
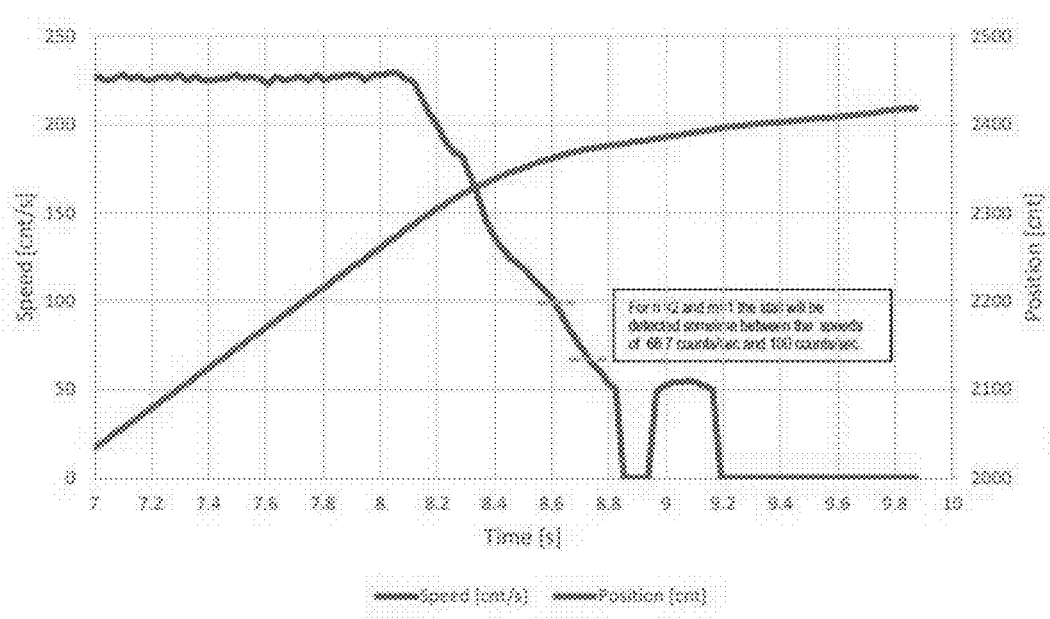
FIG. 16 is a graph showing an extrusion process for an autoinjector device.

When the detection ranges shown in Table 1 are applied to actual data from an injection operation of an autoinjector device 300, as illustrated in FIG. 16, it can be determined how effective the detection algorithm can be. As shown, the injection speed is generally constant at about 225 cnt/s for about 8.1 seconds until the plunger 264 reaches the end of the syringe barrel 261. Thereafter, the speed falls off steadily until the plunger 264 cannot compress anymore, which happens at a little over 8.8 seconds. A little before 9 seconds, the plunger rod 342 starts to embed within the plunger 264 is again stopped at 9.2 seconds. Driving the plunger rod 342 further after 9.2 seconds could break the glass of the syringe barrel 261. Ideally, an injection operation fully compresses the plunger 264 without embedding it therein. As such, in this example, an ideal operation would stop at around 8.8 seconds. The graph shows the range of detection if n=2 and m=1.

If desired, the microprocessor 350 can further be configured to maintain a generally constant extrusion speed to continuously adjust for conditions or configurations of a particular injector 300. The algorithm first set a current limit for a particular speed target, based on the drug 267, injector 300, user preference, and combinations thereof. While the microprocessor 350 samples the plunger rod 342 position, as set forth above, the microprocessor 350 compares the movement of a current sample to a past sample or samples to determine a rate and change. If the speed is over a target, the current limit is adjusted lower. If the speed is under a target, the current limit is adjusted higher.

Disposal of the Used Cassette and Storing the Autoinjector for Future Use

Once the injection process is complete and the autoinjector system 100 is in the state of block 548 (Wait for Door Close B), the user is expected to remove and disposed of the used cassette 200 and close the cassette door 308 of the autoinjector 300 at arrow 550. In order to force the user to do this, the autoinjector system 100 logic may be configured so that the user cannot close the cassette door 308 of the autoinjector 300 with a cassette 200 in the state of block 548. If door closure is attempted at arrow 552, the autoinjector system 100 may detect the cassette 200 and immediately reopen the door at block 554. This may force the user to close the cassette door 308 without a cassette 200 in order for the autoinjector system 100 to move to the state of block 550 (Off) and store the autoinjector 300 for future use. If the user chooses not to perform the required action, the autoinjector system 100 may continue to remain in the same state in block 556 (Door Open Sleep B).

Drug Information

The above description describes various assemblies, devices, and methods for use with a drug delivery device. It should be clear that the assemblies, drug delivery devices, or methods can further comprise use of a drug or medicament listed below with the caveat that the following list should neither be considered to be all inclusive nor limiting. The drug or medicament will be contained in a reservoir. In some instances, the reservoir is a primary container that is either filled or pre-filled for treatment with the drug or medicament. The primary container can be a cartridge or a pre-filled syringe. As used herein, the term drug can be used interchangeably with other similar types of phrases and can be used to mean any type of medicament, therapeutic or non-therapeutic injectable such as traditional and non-traditional pharmaceuticals, nutraceuticals, nutritional supplements, prodrugs (e.g., a compound or molecule which is administered in an inactive or less active state but is cleaved/processed to form the active drug inside the recipient), biologics, biologically active compounds, biologically active molecules, biologically active agents, etc.

The drug container of the cassette may be filled for treatment or be prefilled with a pharmaceutical product, such as an erythropoiesis stimulating agent (ESA), which may be in a liquid or a lyophilized form. An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins comprise erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins comprise, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (comprising EMP1/Hematide), and mimetic antibodies. Exemplary erythropoiesis stimulating proteins comprise erythropoietin, darbepoetin, erythropoietin agonist variants, and peptides or antibodies that bind and activate erythropoietin receptor.

The term erythropoiesis stimulating protein comprises without limitation Epogen® (epoetin alfa), Aranesp® (darbepoetin alfa), Dynepo® (epoetin delta), Mircera® (methoxy polyethylene glycol-epoetin beta), Hematide™ (peginesatide), MRK-2578, INS-22, Retacrit® (epoetin zeta), Neorecormon® (epoetin beta), Silapo™ (epoetin zeta), Binocrit® (epoetin alfa), epoetin alfa Hexal, Abseamed™ (epoetin alfa), Ratioepo™ (epoetin theta), Eporatio™ (epoetin theta), Biopoin™ (epoetin theta), epoetin alfa, epoetin beta, epoetin zeta, epoetin theta, and epoetin delta.

The term erythropoiesis stimulating protein further comprises the molecules or variants or analogs as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,830,851; 5,856,298; 5,955,422; 5,986,047; 6,030,086; 6,310,078; 6,391,633; 6,583,272; 6,586,398; 6,900,292; 6,750,369; 7,030,226; 7,084,245; and 7,271,689; U.S. Publ. Nos. 2002/0155998; 2003/0077753; 2003/0082749; 2003/0143202; 2003/0215444; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0040858; 2006/0088906; and 2006/0111279; and PCT Publ. Nos. WO 91/05867; WO 95/05465; WO 96/40772; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and WO 2007/136752.

Alternatively, the drug container of the cassette may also be filled for treatment or be prefilled with other products. Examples of other pharmaceutical products that may be used may comprise, but are not limited to, therapeutics such as a biological (e.g., Enbrel® (etanercept, TNF-receptor/Fc fusion protein, TNF blocker), anti-TNF antibodies such as adalimumab, infliximab, certolizumab pegol, and golimumab; anti-IL-12 antibodies such as ustekinumab, other Fc fusions such as CTL4A:Fc also known as abacept; Neulasta® (pegylated filgastrim, pegylated G-CSF, pegylated hu-met-G-CSF), Neupogen® (filgrastim, G-CSF, hu-met-G-CSF), Nplate® (romiplostim), Vectibix® (panitumumab), Sensipar® (cinacalcet), and Xgeva® and Prolia® (each denosamab, AMG 162); as well as other small molecule drugs, a therapeutic antibodies, a polypeptides, proteins or other chemicals, such as an iron (e.g., ferumoxytol, iron dextrans, ferric glyconate, and iron sucrose). The therapeutic may be in liquid form, or reconstituted from lyophilized form.

Among particular illustrative proteins that can be used in the drug container of the cassette are antibodies, peptibodies, pegylated proteins, polypeptides, and related proteins (comprising fusions, fragments, analogs, variants or derivatives thereof) for example, proteins that specifically bind to: OPGL; IL-4 receptor; interleukin 1-receptor 1 ("IL1-R1"); angiopoietin-2 (Ang2); NGF; CD22; IGF-1; B-7 related protein 1 (B7RP1); IL-15; IL-17 Receptor A: IFN gamma; TALL-1; parathyroid hormone ("PTH"); thrombopoietin receptor ("TPO-R"); hepatocyte growth factor ("HGF"); TRAIL-R2; Activin A; TGF-beta; amyloid-beta; c-Kit; $\alpha 4\beta 7$: and IL-23 or one of its subunits; and other therapeutic proteins.

The drug container of the cassette may also be filled for treatment or be prefilled with OPGL specific antibodies, peptibodies, and related proteins, and the like (also referred to as RANKL specific antibodies, peptibodies and the like), comprising fully humanized and human OPGL specific antibodies, particularly fully humanized monoclonal antibodies, comprising but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, comprising the OPGL specific antibodies having either the light chain of SEQUENCE IDENTIFICATION NUMBER: 2 therein as set forth in FIG. 2 therein and/or the heavy chain of SEQUENCE IDENTIFICATION NUMBER:4 therein, as set forth in FIG. 4 therein, each of which is individually and specifically incorporated by reference herein in its entirety fully as disclosed in the foregoing Publication.

The drug container of the cassette may also be filled for treatment or be prefilled with myostatin binding proteins, peptibodies, and related proteins, and the like, comprising myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, comprising but not limited to peptibodies of the mTN8-19 family, comprising those of SEQUENCE IDENTIFICATION NUMBERS: 305-351, comprising TN8-19-1 through TN8-19-40, TN8-19 con1 and TN8-19 con2; peptibodies of the mL2 family of SEQUENCE IDENTIFICATION NUMBERS: 357-383 therein; the mL15 family of SEQUENCE IDENTIFICATION NUMBERS: 384-409; the mL17 family of SEQUENCE IDENTIFICATION NUMBERS: 410-438 therein; the mL20 family of SEQUENCE IDENTIFICATION NUMBERS: 439-446 therein; the mL21 family of SEQUENCE IDENTIFICATION NUMBERS: 447-452 therein; the mL24 family of SEQUENCE IDENTIFICATION NUMBERS: 453-454 therein; and those of SEQUENCE IDENTIFICATION NUMBERS: 615-631 therein, each of which is individually and specifically incorporated by reference herein in their entirety fully as disclosed in the foregoing publication.

The drug container of the cassette may also be filled for treatment or be prefilled with IL-4 receptor specific antibodies, peptibodies, and related proteins, and the like, particularly those that inhibit activities mediated by binding of IL-4 and/or IL-13 to the receptor, comprising those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

The drug container of the cassette may also be filled for treatment or be prefilled with IL1-R1 specific antibodies, peptibodies, and related proteins, and the like, comprising but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as in the aforementioned U.S. publication.

The drug container of the cassette may also be filled for treatment or be prefilled with Ang2 specific antibodies, peptibodies, and related proteins, and the like, comprising but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and comprising but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also comprising anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication.

The drug container of the cassette may also be filled for treatment or be prefilled with NGF specific antibodies, peptibodies, and related proteins, and the like comprising, in particular, but not limited to those described in US Publ. No. 2005/0074821 and U.S. Pat. No. 6,919,426, which are incorporated herein by reference in their entirety particularly as to NGF-specific antibodies and related proteins in this regard, comprising in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

The drug container of the cassette may also be filled for treatment or be prefilled with CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, comprising but not limited to humanized and fully human monoclonal antibodies, particularly comprising but not limited to human CD22 specific IgG antibodies, such as, for instance, a dimer of a human-mouse monoclonal hLL2 gamma-chain disulfide linked to a human-mouse monoclonal hLL2 kappa-chain, comprising, but limited to, for example, the human CD22 specific fully humanized antibody in Epratuzumab, CAS registry number 501423-23-0;

The drug container of the cassette may also be filled for treatment or be prefilled with IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, comprising but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication.

Also among non-limiting examples of anti-IGF-1R antibodies for use in the methods and compositions of the present invention are each and all of those described in: (i) US Publ. No. 2006/0040358 (published Feb. 23, 2006), 2005/0008642 (published Jan. 13, 2005), 2004/0228859

(published Nov. 18, 2004), comprising but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein; (ii) PCT Publ. No. WO 06/138729 (published Dec. 28, 2006) and WO 05/016970 (published Feb. 24, 2005), and Lu et al., 2004, J Biol. Chem. 279:2856-65, comprising but not limited to antibodies 2F8, A12, and IMC-A12 as described therein; (iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003); (iv) US Publ. No. 2005/0084906 (published Apr. 21, 2005), comprising but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein; (v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, comprising but not limited to antibody EM164, resurfaced EM164, humanized EM164, huEM164 v1.0, huEM164 v1.1, huEM164 v1.2, and huEM164 v1.3 as described therein; (vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, comprising but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein; (vii) US Publ. Nos. 2005/0136063 (published Jun. 23, 2005) and 2004/0018191 (published Jan. 29, 2004), comprising but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), comprising but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

The drug container of the cassette may also be filled for treatment or be prefilled with B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, comprising but not limited to antibodies designated therein as follow: 16H (having light chain variable and heavy chain variable sequences SEQUENCE IDENTIFICATION NUMBER:1 and SEQUENCE IDENTIFICATION NUMBER:7 respectively therein); 5D (having light chain variable and heavy chain variable sequences SEQUENCE IDENTIFICATION NUMBER:2 and SEQUENCE IDENTIFICATION NUMBER:9 respectively therein); 2H (having light chain variable and heavy chain variable sequences SEQUENCE IDENTIFICATION NUMBER:3 and SEQUENCE IDENTIFICATION NUMBER:10 respectively therein); 43H (having light chain variable and heavy chain variable sequences SEQUENCE IDENTIFICATION NUMBER:6 and SEQUENCE IDENTIFICATION NUMBER:14 respectively therein); 41H (having light chain variable and heavy chain variable sequences SEQUENCE IDENTIFICATION NUMBER:5 and SEQUENCE IDENTIFICATION NUMBER:13 respectively therein); and 15H (having light chain variable and heavy chain variable sequences SEQUENCE IDENTIFICATION NUMBER:4 and SEQUENCE IDENTIFICATION NUMBER:12 respectively therein), each of which is individually and specifically incorporated by reference herein in its entirety fully as disclosed in the foregoing U.S. Publication.

The drug container of the cassette may also be filled for treatment or be prefilled with IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, comprising peptibodies, comprising particularly, for instance, but not limited to, HuMax IL-15 antibodies and related proteins, such as, for instance, 146B7.

The drug container of the cassette may also be filled for treatment or be prefilled with pharmaceutical compositions comprising antagonistic human monoclonal antibodies against human IL-17 Receptor A. The characterization, cloning, and preparation of IL-17 Receptor A are described in U.S. Pat. No. 6,072,033, issued Jun. 6, 2000, which is incorporated herein by reference in its entirety. The amino acid sequence of the human IL-17RA is shown in SEQUENCE IDENTIFICATION NUMBER:10 of U.S. Pat. No. 6,072,033 (GenBank accession number NM 014339). Such antibodies may comprise those disclosed in WO 2008/054603, which is incorporated by reference in its entirety or the antibodies claimed in U.S. Pat. No. 7,767,206, issued Aug. 3, 2010, and in U.S. Ser. No. 11/906,094, which are incorporated by reference in their entirety.

The drug container of the cassette may also be filled for treatment or be prefilled with IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies comprise those having the heavy chain of SEQUENCE IDENTIFICATION NUMBER: 17 and the light chain of SEQUENCE IDENTIFICATION NUMBER:18; those having the heavy chain variable region of SEQUENCE IDENTIFICATION NUMBER:6 and the light chain variable region of SEQUENCE IDENTIFICATION NUMBER:8; those having the heavy chain of SEQUENCE IDENTIFICATION NUMBER:19 and the light chain of SEQUENCE IDENTIFICATION NUMBER:20; those having the heavy chain variable region of SEQUENCE IDENTIFICATION NUMBER:10 and the light chain variable region of SEQUENCE IDENTIFICATION NUMBER:12; those having the heavy chain of SEQUENCE IDENTIFICATION NUMBER:32 and the light chain of SEQUENCE IDENTIFICATION NUMBER: 20; those having the heavy chain variable region of SEQUENCE IDENTIFICATION NUMBER:30 and the light chain variable region of SEQUENCE IDENTIFICATION NUMBER:12; those having the heavy chain sequence of SEQUENCE IDENTIFICATION NUMBER:21 and the light chain sequence of SEQUENCE IDENTIFICATION NUMBER:22; those having the heavy chain variable region of SEQUENCE IDENTIFICATION NUMBER:14 and the light chain variable region of SEQUENCE IDENTIFICATION NUMBER:16; those having the heavy chain of SEQUENCE IDENTIFICATION NUMBER:21 and the light chain of SEQUENCE IDENTIFICATION NUMBER: 33; and those having the heavy chain variable region of SEQUENCE IDENTIFICATION NUMBER:14 and the light chain variable region of SEQUENCE IDENTIFICATION NUMBER:31, as disclosed in the foregoing US Publication. A specific antibody contemplated is antibody 1119 as disclosed in foregoing US Publication and having a complete heavy chain of SEQUENCE IDENTIFICATION NUMBER:17 as disclosed therein and having a complete light chain of SEQUENCE IDENTIFICATION NUMBER: 18 as disclosed therein.

The drug container of the cassette may also be filled for treatment or be prefilled with TALL-1 specific antibodies, peptibodies, and related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B therein, each of which is individually and specifically incorporated by reference herein in its entirety fully as disclosed in the foregoing US Publications.

The drug container of the cassette may also be filled for treatment or be prefilled with PTH specific antibodies, peptibodies, and related proteins, and the like, such as those described in U.S. Pat. No. 6,756,480, which is incorporated herein by reference in its entirety, particularly in parts pertinent to proteins that bind PTH.

The drug container of the cassette may also be filled for treatment or be prefilled with TPO-R specific antibodies, peptibodies, and related proteins, and the like, such as those described in U.S. Pat. No. 6,835,809, which is herein incorporated by reference in its entirety, particularly in parts pertinent to proteins that bind TPO-R.

The drug container of the cassette may also be filled for treatment or be prefilled with HGF specific antibodies, peptibodies, and related proteins, and the like, comprising those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF.

The drug container of the cassette may also be filled for treatment or be prefilled with TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2.

The drug container of the cassette may also be filled for treatment or be prefilled with Activin A specific antibodies, peptibodies, related proteins, and the like, comprising but not limited to those described in US Publ. No. 2009/0234106, which is herein incorporated by reference in its entirety, particularly in parts pertinent to proteins that bind Activin A.

The drug container of the cassette may also be filled for treatment or be prefilled with TGF-beta specific antibodies, peptibodies, related proteins, and the like, comprising but not limited to those described in U.S. Pat. No. 6,803,453 and US Publ. No. 2007/0110747, each of which is herein incorporated by reference in its entirety, particularly in parts pertinent to proteins that bind TGF-beta.

The drug container of the cassette may also be filled for treatment or be prefilled with amyloid-beta protein specific antibodies, peptibodies, related proteins, and the like, comprising but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQUENCE IDENTIFICATION NUMBER: 8 and a light chain variable region having SEQUENCE IDENTIFICATION NUMBER: 6 as disclosed in the International Publication.

The drug container of the cassette may also be filled for treatment or be prefilled with c-Kit specific antibodies, peptibodies, related proteins, and the like, comprising but not limited to those described in Publ. No. 2007/0253951, which is incorporated herein by reference in its entirety, particularly in parts pertinent to proteins that bind c-Kit and/or other stem cell factor receptors.

The drug container of the cassette may also be filled for treatment or be prefilled with OX40L specific antibodies, peptibodies, related proteins, and the like, comprising but not limited to those described in U.S. application Ser. No. 11/068,289, which is incorporated herein by reference in its entirety, particularly in parts pertinent to proteins that bind OX40L and/or other ligands of the OX040 receptor.

The drug container of the cassette may also be filled for treatment or be prefilled with other exemplary proteins comprising but are not limited to Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Solids™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP IIb/IIIa receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-*B. anthracis* Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Ra mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab), BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2; a sclerostin antibody, such as but not limited to romosozumab, blosozumab, or BPS 804 (Novartis). Also included can be therapeutics such as rilotumumab, bixalomer, trebananib, ganitumab, conatumumab, motesanib diphosphate, brodalumab, vidupiprant, panitumumab, denosumab, romosozumab NPLATE, PROLIA, VECTIBIX or XGEVA. Additionally, included in the Al can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

The drug container of the cassette may also be filled for treatment or be prefilled with antibodies comprising, but not limited to, those that recognize any one or a combination of proteins comprising, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19-25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphylococcus aureus*.

Additional examples of known antibodies that may be contained in the drug container of the cassette can comprise but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, zalutumumab, and zanolimumab.

Although the autoinjector system, cassette, and autoinjector, have been described in terms of exemplary embodiments, it is not limited thereto. Rather, the appended claims should be construed broadly, to comprise other variants and embodiments of same, which may be made by those skilled in the art without departing from the scope and range of equivalents of the autoinjector system, cassette, and autoinjector and their elements.

What is claimed is:

1. A drug delivery device comprising:
   a reservoir configured to contain a drug and having a first end and a second end;
   a plunger disposed within the reservoir at the first end thereof, the plunger slidingly movable within the reservoir;
   a plunger rod configured to engage the plunger;
   a motor operably coupled to the plunger rod and configured to drive the plunger rod to thereby slide the plunger from the first end of the reservoir to the second end of the reservoir;
   an encoder operably coupled to the motor; and
   a controller configured to
   (i) receive signals from the encoder,
   (ii) determine whether the plunger has stopped moving within the reservoir based on the signals, and
   (iii) stop operation of the motor in response to determining that the plunger has stopped moving for a predetermined amount of time.

2. The drug delivery device of claim 1, wherein the encoder includes a disk having one or more discernible portions and an optical sensor configured to detect the discernible portions and send a signal in response to the detection.

3. The drug delivery device of claim 1, wherein a count of the signals is indicative of a position of the plunger rod and the controller is configured to sample the position of the plunger rod at set intervals by determining a current count of the signals.

4. The drug delivery device of claim 3, wherein the controller being configured to determine whether the plunger has stopped moving comprises the controller determining whether the signals indicate that the plunger has moved within a predetermined number of samples of the signals.

5. The drug delivery device of claim 4, wherein the controller is configured to compare the current count to an expected endpoint count corresponding to the plunger being driven to the second end of the reservoir.

6. The drug delivery device of claim 5, wherein the controller is configured to revise the predetermined number of samples in response to determining that the current count is less than the expected endpoint.

7. The drug delivery device of claim 5, wherein the controller is configured to determine that the plunger has stalled in response to determining that the current count is less than the expected endpoint.

8. The drug delivery device of claim 1, further comprising a needle and a needle insertion mechanism, and wherein the controller is configured to cause the needle insertion mechanism to retract the needle in response to determining that the plunger has stopped moving for the predetermined amount of time.

9. The drug delivery device of claim 1, wherein the drug delivery device comprises an autoinjector.

10. The drug delivery device of claim 1, further comprising a drug in the reservoir, wherein the drug comprises etanercept.

11. A method for operating a drug delivery device, the method comprising:
    receiving signals at a controller from an encoder coupled to a motor of the drug delivery device, the motor operably coupled to a plunger rod configured to engage and drive a plunger within a reservoir;
    determining whether the plunger has stopped moving within the reservoir with the controller based on the signals;
    stopping operation of the motor with the controller in response to determining that the plunger has stopped moving for a predetermined amount of time.

12. The method of claim 11, further comprising:
    detecting a discernible portion of a disk of the encoder with an optical sensor; and
    sending a signal in response to the detection.

13. The method of claim 11, further comprising sampling a position of the plunger rod at set intervals with the controller by determining a current count of the signals.

14. The method of claim 13, wherein determining whether the plunger has stopped moving within the reservoir comprises determining whether the signals indicate that the plunger has moved within a predetermined number of samples of the signals.

15. The method of claim 14, further comprising comparing the current count to an expected endpoint count corresponding to the plunger being driven to a second end of the reservoir.

16. The method of claim 15, further comprising revising the predetermined number of samples in response to determining that the current count is less than the expected endpoint.

17. The method of claim 15, further comprising determining that the plunger has stalled before being driven to the second end of the reservoir in response to determining that the current count is less than the expected endpoint.

18. The method of claim 11, further comprising retracting a needle of the drug delivery device with a needle insertion mechanism in response to the controller determining that the plunger has stopped moving for the predetermined amount of time.

19. The method of claim 11, wherein the drug delivery device comprises an autoinjector.

* * * * *